(12) United States Patent
Liu et al.

(10) Patent No.: US 11,993,627 B2
(45) Date of Patent: May 28, 2024

(54) ENZYMATIC SYNTHESIS OF HOMOGENEOUS CHONDROITIN SULFATE OLIGOSACCHARIDES

(71) Applicant: The University of North Carolina at Chapel Hill, Chapel Hill, NC (US)

(72) Inventors: Jian Liu, Chapel Hill, NC (US); Jine Li, Chapel Hill, NC (US); Guowei Su, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 162 days.

(21) Appl. No.: 16/625,342

(22) PCT Filed: Jul. 3, 2018

(86) PCT No.: PCT/US2018/040774
§ 371 (c)(1),
(2) Date: Dec. 20, 2019

(87) PCT Pub. No.: WO2019/010216
PCT Pub. Date: Jan. 10, 2019

(65) Prior Publication Data
US 2021/0332076 A1  Oct. 28, 2021

Related U.S. Application Data

(60) Provisional application No. 62/528,243, filed on Jul. 3, 2017.

(51) Int. Cl.
*C07H 3/06* (2006.01)
*C07H 11/00* (2006.01)
(Continued)

(52) U.S. Cl.
CPC ............... *C07H 3/06* (2013.01); *C07H 11/00* (2013.01); *C08B 37/0063* (2013.01);
(Continued)

(58) Field of Classification Search
None
See application file for complete search history.

(56) References Cited

U.S. PATENT DOCUMENTS 4,554,101 A   11/1985  Hopp
4,865,870 A   9/1989   Hu et al.
(Continued)

FOREIGN PATENT DOCUMENTS

CN   110446511 A   11/2019
CN   105452479 B   5/2021
(Continued)

OTHER PUBLICATIONS

Sugumaran et al., "Simultaneous Sulfation of endogenous Chondroitin Sulfate and Chondroitin-derived Oligosaccharides" The Journal of Biological Chemistry vol. 261 No. 27 pp. 12659-12664 (Year: 1986).*
(Continued)

*Primary Examiner* — Eric Olson
(74) *Attorney, Agent, or Firm* — Jenkins, Taylor & Hunt, P.A.

(57) ABSTRACT

Methods of synthesizing chondroitin sulfate oligosaccharides are provided. Enzymatic schematic approaches to synthesizing structurally defined homogenous chondroitin sulfate oligosaccharides at high yields are provided. Synthetic chondroitin sulfate oligosaccharides ranging from 3-mers to 15-mers are provided.

8 Claims, 12 Drawing Sheets

(51) Int. Cl.
- *C08B 37/00* (2006.01)
- *C12N 9/10* (2006.01)
- *C12P 19/26* (2006.01)

(52) U.S. Cl.
CPC ........ *C08B 37/0069* (2013.01); *C12N 9/1048* (2013.01); *C12N 9/13* (2013.01); *C12P 19/26* (2013.01)

(56) References Cited

U.S. PATENT DOCUMENTS

| | | |
|---|---|---|
| 5,527,785 A | 6/1996 | Bevilacqua |
| 5,543,403 A | 8/1996 | Petitou et al. |
| 5,817,487 A | 10/1998 | Kobayashi et al. |
| 5,834,282 A | 11/1998 | Habuchi et al. |
| 5,935,824 A | 8/1999 | Sgarlato |
| 6,255,088 B1 | 7/2001 | Wong et al. |
| 6,861,254 B1 | 3/2005 | Rosenberg et al. |
| 7,101,859 B2 | 9/2006 | Yedgar et al. |
| 7,531,338 B2 | 5/2009 | Liu |
| 9,951,149 B2 | 4/2018 | Liu et al. |
| 10,286,047 B2 | 5/2019 | Spirig et al. |
| 11,203,772 B2 | 12/2021 | Xu et al. |
| 11,633,424 B2 * | 4/2023 | Liu .......................... A61P 31/04 514/54 |
| 2003/0083294 A1 | 5/2003 | Sullenger |
| 2003/0099967 A1 | 5/2003 | Deangelis |
| 2004/0191870 A1 | 9/2004 | Rosenberg et al. |
| 2004/0259142 A1 | 12/2004 | Chai et al. |
| 2005/0090601 A1 * | 4/2005 | Dadalas ............... C09D 127/18 524/544 |
| 2005/0090661 A1 | 4/2005 | Asari et al. |
| 2005/0101532 A1 | 5/2005 | Yang et al. |
| 2005/0191288 A1 | 9/2005 | Bennett et al. |
| 2005/0255562 A1 | 11/2005 | Rosenberg et al. |
| 2005/0282775 A1 | 12/2005 | Kennedy |
| 2006/0165673 A1 | 7/2006 | Liu |
| 2006/0172931 A1 | 8/2006 | San Antonio et al. |
| 2006/0229276 A1 | 10/2006 | Hook et al. |
| 2008/0109236 A1 | 5/2008 | DeAngelis |
| 2009/0035787 A1 | 2/2009 | Liu |
| 2009/0155851 A1 * | 6/2009 | Sugiura ................... C12P 19/26 536/18.7 |
| 2009/0197308 A1 | 8/2009 | Liu |
| 2010/0125052 A1 | 5/2010 | Lu et al. |
| 2010/0298260 A1 | 11/2010 | Sundaram et al. |
| 2010/0305022 A1 | 12/2010 | Shriver |
| 2011/0054236 A1 | 3/2011 | Yang et al. |
| 2011/0281819 A1 | 11/2011 | Kakehi et al. |
| 2012/0064044 A1 | 3/2012 | Egan |
| 2012/0308546 A1 | 12/2012 | Kizhakkedathu et al. |
| 2012/0322114 A1 | 12/2012 | Liu et al. |
| 2012/0322760 A1 | 12/2012 | Fier et al. |
| 2013/0022647 A1 | 1/2013 | Kizhakkedathu et al. |
| 2013/0296540 A1 | 11/2013 | Xu et al. |
| 2013/0338097 A1 | 12/2013 | Stephens et al. |
| 2016/0122446 A1 | 5/2016 | Liu et al. |
| 2021/0137967 A1 | 5/2021 | Liu et al. |
| 2021/0169923 A1 | 6/2021 | Arnold et al. |
| 2021/0260098 A1 * | 8/2021 | Liu .......................... A61P 31/04 |
| 2022/0265699 A1 | 8/2022 | Arnold et al. |
| 2022/0416486 A1 | 12/2022 | Yamaguchi |
| 2023/0277580 A1 | 9/2023 | Liu et al. |

FOREIGN PATENT DOCUMENTS

| | | |
|---|---|---|
| EP | 0 394 971 | 10/1990 |
| EP | 0 565 863 | 10/1993 |
| JP | 6670235 | 3/2020 |
| JP | 7330893 | 8/2023 |
| WO | WO 89/04328 | 5/1989 |
| WO | WO93/05167 | 3/1993 |
| WO | WO 96/14425 | 5/1996 |
| WO | WO2003018598 | 3/2003 |
| WO | WO 2004/005475 A2 | 1/2004 |
| WO | WO 2004/009642 | 1/2004 |
| WO | WO 2004/017910 A2 | 3/2004 |
| WO | WO2005/118609 | 12/2005 |
| WO | WO 2006/124801 | 11/2006 |
| WO | WO 2009/079693 A1 | 7/2009 |
| WO | WO 2012/088416 A2 | 6/2012 |
| WO | WO 2012/116048 | 8/2012 |
| WO | WO 2014/204929 | 12/2014 |
| WO | WO 2018/165656 | 9/2018 |
| WO | WO 2019/090203 A1 | 5/2019 |
| WO | WO 2019/246264 | 12/2019 |
| WO | WO 2021/097345 A1 | 5/2021 |

OTHER PUBLICATIONS

Coutant et al., "2-Deoxy-2-trichloroacetamido-D-glucopyranose derivatives in oligosaccharide synthesis: from hyaluronic acid to chondroitin 4-sulfate trisaccharides" J Chem Soc Perkin Trans 1 (1995) 1573-1581 (Year: 1995).*

Takagaki et al., "Enzymatic Reconstruction of a Hybrid Glycosaminoglycan Containing 6-Sulfated, 4-Sulfated, and Unsulfated N-Acetylgalactosamine" Biochemical and Biophysical Research Communications vol. 258 pp. 741-744 (Year: 1999).*

Belot et al., "Syntheses of chondroitin 4- and 6-sulfate pentasaccharide derivatives having a methyl beta-D-glucopyranosiduronic acid at the reducing end" Carbohydrae Research vol. 326 pp. 88-97 (Year: 2000).*

Beeson et al., "Inhibition of Binding of Malaria-Infected Erythrocytes by a Tetradecasaccharide Fraction from Chondroitin Sulfate A" Infection and Immunity vol. 66 No. 7 pp. 3397-3402 (Year: 1998).*

U.S. Appl. No. 18/138,596, filed Apr. 2023, Liu; Jian.*

Tamura et al., "Synthetic approach towards sulfated chondroitin di-, tri- and tetrasaccharides corresponding to the repeating unit" Carbohydrate Research vol. 305 pp. 43-63 (Year: 1998).*

Sugiura et al., "Sequential synthesis of chondroitin oligosaccharides by immobilized chondroitin polymerase mutants" Glycoconjugate Journal vol. 25 pp. 521-530 (Year: 2008).*

Takagaki et al., "Chimeric Glycosaminoglycan Oligosaccharides Synthesized by Enzymatic Reconstruction and Their Use in Substrate Specificity Determination of *Streptococcus hyaluronidase*" J Biochem vol. 127 pp. 695-702 (Year: 2000).*

Decision to Grant corresponding to Japanese Patent Application Serial No. 18/138,596 dated Jul. 5, 2023.

Notice of Publication corresponding to U.S. Appl. No. 18/138,596 dated Sep. 7, 2023.

Office Action corresponding to U.S. Appl. No. 16/625,342 dated Jun. 15, 2023.

Advisory Action corresponding to U.S. Appl. No. 13/996,930 dated Dec. 9, 2016.

Aikawa et al., "Molecular Cloning and Expression of a Third Member of the Heparan Sulfate/Heparin GlcNAc N-Deacetylase/N-Sulfotransferase Family," The Journal of Biological Chemistry, vol. 274, No. 5, pp. 2690-2695 (Jan. 29, 1999).

Aikawa et al., "Multiple Isozymes of Heparan Sulfate/Heparin GlcNAc N-Deacetylase/GlcN N-Sulfotransferase," The Journal of Biological Chemistry, vol. 276, No. 8, pp. 5876-5882 (Feb. 23, 2001).

Alexander et al., "Syndecan-1 is required for Wnt-1-induced mammary tumorigenesis in mice," Nat. Genet., vol. 25, pp. 329-332 (2000).

Altschul et al., "Basic Local Alignment Search Tool," J. Mol Bio., vol. 1215, pp. 403-410 (1990).

Antoine et al., "Mechanistic biomarkers provide early and sensitive detection of acetaminophen-induced acute liver injury at first presentation to hospital." Hepatology vol. 58, pp. 777-787 (2013).

Applicant-Initiated Interview Summary corresponding to U.S. Appl. No. 13/996,930 dated Jan. 23, 2017.

Arnold et al., "Design of anti-inflammatory heparan sulfate to protect against acetaminophen-induced acute liver failure." Sci. Transl. Med., vol. 12, Article ID eaav8075 (2020).

(56) References Cited

OTHER PUBLICATIONS

Arnold et al., "Synthetic anticoagulant heparan sulfate attenuates liver ischemia reperfusion injury." Sci. Reports, vol. 10, Article No. 17187 (10 pages) (2020).
Arnold, Biomedicines 2020, 8, 0503. (Year: 2020).
Arungundram, S.; Al-Mafraji, K.; Asong, J.; Leach III, F. E.; Amster, I. J.; Venot, A.; Je, T.; Boons, G. J. "Modular Synthesis of Heparan Sulfate Oligosaccharides for Structure-Activity Relationship Studies," J. Am. Chem. Soc. 2009, 131, 17394.
Atha et al., "Contribution of Monosaccharide Residues in Heparin Binding to Antithrombin III," Biochemistry, vol. 24, pp. 6723-6729 (1985).
Avci et al., "Synthetic oligosaccharides as heparin-mimetics displaying anticoagulant properties," Curr. Pharm. Des., vol. 9, pp. 2323-2335 (2003).
Axelsson et al., "Inactivation of heparan sulfate 2-O-sulfotransferase accentuates neutrophil infiltration during acute inflammation in mice." Blood, vol. 120, pp. 1742-1751 (2012).
Bailey et al., "Delays during the administration of acetylcysteine for the treatment of paraacetamol overdose." Br. J. Clin. Pharmacol. vol. 62, pp. 1358-1363 (2016).
Balagurunathan et al., Chemoenzymatic Synthesis of Classical and Non-classical Anticoagulant Heparan Sulfate Polysaccharide, J. Biol. Chem., vol. 278, pp. 52613-52621 (2003).
Balagurunathan et al., Enzymatic synthesis of antithrombin III-binding heparan sulfate pentasaccharide, Nat. Biotechnol., vol. 21, pp. 1343-1346 (2003).
Baleux et al. (2009) Nat. Chem. Biol., 5, 743-748.
Bernfield et al., "Heparin-Binding Proteins," Annu. Rev. Biochem., vol. 68, pp. 729-777 (1999).
Bianchi et al., "High-mobility group box 1 protein orchestrates responses to tissue damage via inflammation, innate and adaptive immunity, and tissue repair." Immunol. Rev. Vol. 280, pp. 74-82 (2017).
Bitter et al. (1962) Anal. Biochem. 4, 330-334.
Bjornsson, Simultaneous Preparation and Quantitation of Proteoglycans by Preciptation with Alcian Blue, Anal. Biochem., vol. 210, pp. 282-291 (1993).
Blieden et al., "A perspective on the epidemiology of acetaminophen exposure and toxicity in the United States." Expert Rev. Clin. Pharmacol. Vol. 7, pp. 341-348 (2014).
Bourgeaux et al., "Two-step enzymatic synthesis of UDP-N-acetylgalactosamine." Bioorg. Med. Chem. Lett., vol. 15, pp. 5459-5462 (2005).
Bowman et al., Carbohydrate sulfotransferases: medliators of extracellular Communication, Chemistry & Biology, vol. 6, pp. R9-R22 (Jan. 1999).
Bradbury et al., "Chondroitinase ABC promotes functional recovery after spinal cord injury." Nature, vol. 416, pp. 636-640 (2002).
Brinkmann V, Reichard U, Goosmann C, Fauler B, Uhlemann Y, Weiss DS, et al. Neutrophil extracellular traps kill bacteria. Science. 2004;303:1532-5.
Broun et al., "Catalytic plasticity of fatty acid modification enzymes underlying chemical diversity of plant lipids," Science, vol. 282, pp. 1315-1317 (1998).
Brown et al., "A sulfated carbohydrate epitope inhibits axon regeneration after injury." Proc. Natl. Acad. Sci. USA, vol. 109, pp. 4768-4773 (2012).
Brown et al., Drug Research, "Cardenolide analogues. 11. Improved method for the use of Fetizon's reagent in the synthesis of cardiac glycosides", vol. 31, No. 7, pp. 1059-1064 (1981).
Burkart et al., "Regeneration of PAPS for the Enzymatic Synthesis of Sulfated Oligosaccharides," J. Org. Chem., vol. 65, pp. 5565-5574 (2000).
Cai et al., "Towards the chemoenzymatic synthesis of heparan sulfate oligosaccharides: Oxidative cleavage of p-nitrophenyl group with ceric ammonium salts," Tetra. Lett., vol. 54, No. 33, pp. 4471-1474 (2013).
Capila et al., "Heparin—Protein Interactions," Angew. Chem. Int. Ed., vol. 41, pp. 390-412 (2002).

Carfi et al., "Herpes Simplex Virus Glycoprotein D Bound to the Human Receptor HveA," Molecular Cell, vol. 8, pp. 169-179 (Jul. 2001).
Cassinelli et al., "Old and new applications of non-anticoagulant heparin." International Journal of Cardiology, 212S1 pp. S14-S21 (2016).
Casu et al., Heparin-like compounds prepared by chemical modification of capsular polysaccharide from $E.\ coli$ K5, Carbohydrate Research vol. 263, pp. 271-28 (1994).
Chan et al., "Regulation of PfEMP1-VAR2CSA translation by a Plasmodium translation-enhancing factor." Nature Microbiology, vol. 2, Article No. 17068 (2017).
Chen et al., "Enzymatic redesigning of biologically active haparan sulfate," JBC, vol. 280, No. 52, pp. 42817-42825 (2005).
Chen et al., "Using an Enzymatic Combinatorial Approach to Identify Anticoagulant Heparan Sulfate Structures." Chemistry and Biology, Current Biology, London, GB, vol. 14., No. 9, pp. 986-993 (Sep. 19, 2007).
Chen et al., "Biosynthesis of 3-O-sulfated heparan sulfate: unique substrate specificity of heparan sulfate 3-O-sulfotransferase isoform 5," Glycobiology, vol. 13, No. 11, pp. 785-794 (Nov. 2003).
Chen et al., "Sterile inflammation: sensing and reacting to damage." Nat. Immunol. Vol. 10, pp. 826-837 (2010).
Chen et al., Towards De Novo Synthesis of Structure-Defined Oligosaccharides with Heparan Sulfate Biosynthetic Enzymes, PhD dissertation,pp. 1-167, (Date Created: Aug. 2008; Date Deposited: Oct. 11, 2010.).
Chen et al., "Tyrosine-Ester Sulfotransferase from Rat Liver: Bacterial Expression and Identificationn," Protein Expression Purif., vol. 3, pp. 421-426 (1992).
Chen, M., et al. (2006) Biochemistry, 45, 12358-12365.
Chinese International Search Report Corresponding to Chinese Application No. 2020800928292.2 dated Nov. 13, 2020.
Clark SR, Ma AC, Tavener SA, McDonald B, Goodarzi Z, Kelly MM, et al. Platelet TLR4 activates neutrophil extracellular traps to ensnare bacteria in septic blood. Nat Med. 2007; 13:463-9.
Communication of European publication number and information on the application of Article 67(3) EPC corresponding to European Application No. 14812890.3 dated Mar. 31, 2016.
Communication of European publication number corresponding to European Patent application No. 20887629.2 dated Jul. 20, 2022.
Communication of the extended European search report corresponding to European Application No. 14812890.3 dated Dec. 21, 2016.
Conrad, Heparin-Binding Proteins, J. of Medicinal Chemistry, vol. 42, No. 4, pp. 777-778 (1998).
Copeland et al., "Using a 3-O-Sulfated Heparin Octasaccharide to Inhibit the Entry of Herpes Simplex Virus Type 1," Biochemistry, vol. 47, pp. 5774-5783 (2008).
Corrected Notice of Allowability corresponding to U.S. Appl. No. 16/492,858 dated Sep. 20, 2022.
Corrected Notice of Allowance corresponding to U.S. Appl. No. 16/492,858 dated Sep. 20, 2022.
Crowther et al., "Mechanisms responsible for the failure of protamine to inactivate low-molecular-weight heparin," British Journal of Hematology, vol. 116, pp. 178-186 (2002).
Darden, T.; York, D.; Pedersen, L. C. J. Chem. Phys. 1993, 98, 10089.
Das et al., "Synthesis of Conformationally Locked I-Iduronic Acid Derivatives: Direct Evidence for a Critical Role of the Skew-Boat 2S0 Conformer in the Activation of Antithrombin by Heparin," Chem. Eur. J., vol. 7, No. 22, pp. 4821-4834 (2001).
Davenport, "Review article: Low-molecular-weight heparin as an alternative anticoagulant to unfractionated heparin for routine outpatient haemodialysis treatments," Nephrology, vol. 14, pp. 456-461 (2009).
Deagostini, A. I.; Dong, J .-C.; de Vantery Arrighi, C.; Ramus, M.-A.; Dentand-Quadri, I.; Thanlmann, S.; Ventura, P.; Ibecheole, V.; Monge, F.; Fischer, A .-M.; HajMohammadi, S.; Shworak, N.; Zhang, L.; Zhang, Z.; Linhardt , R. J. "Human Follicular Fluid Heparan Sulfate Contains Abundant 3-O-Sulfated Chains with Anticoagulant Activity," J. Biol. Chem. 2008, 283, 28115.
Decision to Grant corresponding to Japanese Patent Application No. 2016521505 dated Feb. 3, 2020.

(56) References Cited

OTHER PUBLICATIONS

Decision to Grant corresponding to Japanese Patent Application No. 2019549419 dated Jul. 11, 2023.
Dementiev et al., "The ternary complex of antithrombin-anhydrothrombin-heparin reveals the basis of inhibitor specificity," Nat. Struct. Biol., vol. 11, pp. 867-863 (2004).
Dooley, T., "Cloning of the human phenol sulfotransferase gene family: three genes implicated in the metabolism of catecholamines, thyroid hormones and drugs," Chemico-Biological Interactions, vol. 109, pp. 29-41 (1998).
Dou et al., "Role of Deacetylase Activity of N-Deacetylase/N-Sulfotransferase 1 in Forming N-Sulfated Domain in Heparan Sulfate", The Journal of Biological Chemistry, vol. 290, No. 33, pp. 20427-20437 (Aug. 14, 2015).
Duncan et al., Biochim. Biophys. Acta, vol. 1671, pp. 34-43 (2004).
Edavettal et al.,, "Crystal Structure and Mutational Analysis of Heparan Sulfate 3-O-Sulfotransferase Isoform 1," J. Biol. Chem., vol. 279, No. 24, pp. 25789-25797 (Jun. 11, 2004).
Edens et al., "Gradient Polyacrylamide Gel Electrophoresis for Determination of Molecular Weights of Heparin Preparations and Low-Molecular-Weight Heparin Derivatives," J. Pharm. Sci., vol. 81, No. 8, pp. 823-827 (Aug. 1992).
Eller et al., "Automated Solid-Phase Synthesis of Chondroitin Sulfate Glycosaminoglycans." Angew. Chem. Int. Ed., vol. 52, pp. 5858-5861 (2013).
Esko et al., "Molecular diversity of heparan sulfate," J. Clin. Invest., vol. 108, pp. 169-173 (2001).
Esko et al., "Order Out of Chaos: Assembly of Ligand Binding Sites in Heparan Sulfate," Annu. Rev. Biochem., vol. 71, pp. 435-471 (2002).
European Search Report corresponding to European Patent Application No. 18764628.6 dated Dec. 2, 2020.
European Search Report corresponding to European Patent Application No. 18873131.9 dated Jul. 12, 2021.
Extended European Search Report Corresponding to European Patent Application No. 19822610.2 dated Mar. 29, 2022.
Falany, C., "Introduction: Changing view of sulfation and the cytosolic Sulfotransferases," vol. 11, The FASEB Journal, pp. 1-2 (Jan. 1997).
Feltracco et al., "Perioperative thrombotic complications in liver transplantation." World J. Gastroenterol., vol. 21, pp. 8004-8013 (2015).
Feng et al., "Characteristics Associated with Liver Graft Failure: The Concept of a Donor Risk Index." Am. J. Transplant., vol. 6, pp. 783-790 (2006).
Feyerabend et al., "Heparan sulfate C5-epimerase is essential for heparin biosynthesis in mast cells," Nat. Chem. Biol., vol. 2, No. 4, pp. 195-196 (Apr. 2006).
Fiser, A; Sali, A Methods Enzymol 2003, 374, 461.
Frank, Thromb Haemost 2006; 96:802-6. (Year: 2006).
Freeman et al., "The accumulation of circulating histones on heparan sulphate in the capillary glycocalyx of the lungs." Biomater., vol. 34, pp. 5670-5676 (2013).
Fried et al., "Designing a VAR2CSA-based vaccine to prevent placental malaria." Vaccine, vol. 33, pp. 7483-7488 (2015).
Fukuta et al., "Molecular cloning and expression of human chondroitin 6-sulfotransferase," Biochimica et Biophysica Acta, vol. 1399, pp. 57-61 (1998).
Fuster et al., The sweet and sour of cancer: glycans as novel therapeutic targets, Nat. Rev. Cancer, vol. 5, No. 7, pp. 1-27 (Jul. 2005).
Gallagher, "Heparan sulfate: growth control with a restricted sequence menu," J. Clin. Invest., vol. 108, pp. 357-361 (2001).
Gama et al., "Sulfation patterns of glycosaminoglycans encode molecular recognition and activity," Nat. Chem. Biol., vol. 2, No. 9, pp. 467-473 (Sep. 2006).
Ganey et al. "Role of the Coagulation System in Acetaminophen-Induced Hepatotoxicity in Mice." Hepatology, vol. 46(4), pp. 1177-1186 (2007).
Genbank Accession No. AAC40135 dated Jun. 17, 1998.
Genbank Accession No. BAA89247 dated Jan. 29, 2000.
Genbank Accession No. NP_005105 dated May 24, 2014.
Genbank Accession No. NP_006032 dated Feb. 26, 2014.
Genbank Accession No. NP_006033 dated Jan. 26, 2014.
Genbank Accession No. NP_056633 dated May 3, 2014.
Genbank Accession No. NP_056635 dated Mar. 3, 2014.
Gribskov,M., Burgess, R.R. and Devereux,J. (1986) Nucl. Acids Res. 14, 327-334.
Guerrini et al., "Oversulfated chondroitin sulfate is a contaminant in heparin associated with adverse clinical events," Nat. Biotechnol., vol. 26, No. 6, pp. 669-675 (Jun. 2008).
Guerrini, M.; Elli, S.; Mourier, P.; Rudd, T. R.; Gaudesi, D.; Casu, B.; Boudier, C.; Torri, G.; Viskov, C. "An unusual antithrombin-binding heparin octasaccharide with an additional 3-O-sulfated glucosamine in the active pentasaccharide sequence," Biochem. J. 2013, 449, 343.
Guerrini, M.; Mourier, P. A.; Torri, G.; Viskov, C. "Antithrombin-binding oligosaccharides: structural diversities in a unique function?," Glycoconj. J. 2014, 31, 409.
Guimond et al., "Fibroblast growth factor receptor signaling is dictated by specific heparin sulphate saccharides," Curro. Biol., vol. 9, No. 22 pp. 1343-1346 (1999).
Guo et al., "Changes in substrate specificity of the recombinant form of phenol sulfotransferase IV (tyrosine-ester sulfotransferase)," Chem.-Biol. Interact., vol. 92, pp. 25-31 (1994).
Habuchi et al., The Occurrence of Three Isoforms of Heparan Sulfate 6-O-Sulfotransferase Having Different Specificities for Hexuronic Acid Adjacent to the Targeted N-Sulfoglucosamine, J. Biol. Chem., vol. 275, No. 4, pp. 2859-2868 (Jan. 28, 2000).
Habuchi et al., "Molecular Characterization and Expression of Heparan-sulfate 6-Sulfotransferase—Complete cDNA Cloning in Human and Partial Cloning in Chinese Hamster Ovary Cells," The Journal of Biological Chemistry, vol. 273, No. 15, pp. 9208-9213 (Apr. 10, 1998).
Habuchi et al., "Purification of Chondroitin 6-Sulfotransferase Secreted from Cultured Chick Embryo Chondrocytes," The Journal of Biological Chemistry, vol. 268(29), pp. 21968-21974 (1993).
Hajmohammadi, S.; Enjyoji, K.; Princivalle, M.; Christi, P.; Lech, M.; Beeler, D. L.; Rayburn, H.; Schwartz, J. J.; Barzegar, S.; de Agostini, A. I.; Post, M. J.; Rosenberg, R. D.; Shworak, N. W. J. Clin. Invest. 2003, 111, 989.
Hansen, S. U.; Miller, G. J.; Cole, C.; Rushton, G.; Avizienyte, E.; Jayson, G. C.; Gardiner, J. M. Nat Commun 2013, 4:2016, doi:10.1038/ncomms3016.
Harada et al., "Dalteparin, a low molecular weight heparin, attenuates inflammatory responses and reduces ischemia-reperfusion-induced liver injury in rats." Crit. Care Med., vol. 34, Article No. 8, (2006).
Harris et al., Endocytic Function, Glycosaminoglycan Specificity, and Antibody Sensitivity of the Recombinant Human 190-kDa Hyaluronan Receptor for Endocytosis (HARE), J. Biol. Chem., vol. 279, No. 35, pp. 36201-36209 (Aug. 27, 2004).
Heard, "Acetylcystein for acetaminophen poisoning." N. Eng. J. Med. vol. 359, pp. 285-292 (2008).
Hernaiz et al., "Enzymatic Modification of Heparan Sulfate on a Biochip Promotes Its Interaction with Antithrombin III," Biochem. Biophys. Res. Commun., vol. 276, pp. 292-297 (2000).
Hirsch et al., Heparin and Low-Molecular-Weight Heparin the Seventh ACCP Conference on Antithrombotic and Thrombolytic Therapy, CHEST, vol. 126, pp. 188S-203S (2004).
Hirsh et al., "Beyond Unfractionated Heparin and Warfarin Current and Future Advances," Circulation, vol. 116, pp. 552-560 (2007).
Holmborn et al., "Heparan Sulfate Synthesized by Mouse Embryonic Stem Cells Deficient in NDST1 and NDST2 Is 6-O-Sulfated but Contains No N-Sulfate Groups," J. Biol. Chem., vol. 279, No. 41, pp. 42355-42358 (2004).
Hsieh et al., "Chemoenzymatic synthesis and structural characterization of 2-O-sulfated glucuronic acid containing heparan sulfate hexasaccharides." Glycobiology vol. 24, pp. 681-692 (2014).
Hsieh, P.- H.; Thieker, D. F.; Guerrini, M.; Woods, R. J.; Liu, J. Sci Rep 2016, 6, 29602; doi: 10.1038/srep29602.
Hu, Y.-P.; Lin, S.-Y.; Huang, C.-Y.; Zulueta, M. M. L.; Liu, J.-Y.; Chang, W.; Hung, S.-C. Nat Chem 2011. 3, 557.

(56) References Cited

OTHER PUBLICATIONS

Huang, C. C.; Meng, E. C.; Morris, J. H.; Pettersen, E. F.; Ferrin, T. E. Nucleic Acids Res. 2014, 42, w478.
Huebener el al., "The HMGB1/RAGE axis triggers neutrophil-mediated injury amplification following necrosis." J. Clin. Invest. vol. 125, pp. 539-550 (2015).
Humphrey, W.; Dalke, A; Schulten, K. J. Mol. Graph. 1996, 14, 33.
Iba et al., "Advance in the management of sepsis-induced coagulopathy and disseminated intravascular coagulation." J. Clin. Med., vol. 8, Article No. 728 (16 pages) (2019).
Ibrahimi et al., "Kinetic Model for FGF, FGFR, and Proteoglycan Signal Transduction Complex Assembly," Biochemistr, vol. 43, pp. 4724-4730 (2004).
Intention to Grant corresponding to European Patent Application No. 11849994.6 dated Apr. 7, 2021.
Intention to Grant corresponding to European Patent Application No. 11849994.6 dated Sep. 1, 2021.
Intention to Grant corresponding to European Patent Application No. 14812890.3 dated Oct. 27, 2021.
International Preliminary Report on Patentability corresponding to International Application No. PCT/US2018/040774 dated Jan. 16, 2020.
International Preliminary Report on Patentability corresponding to International Application No. PCT/US2019/037993 dated Dec. 22, 2020.
International Preliminary Report on Patentability Corresponding to International Patent Application No. PCT/US 2020/060581 dated May 27, 2022.
International Preliminary Report on Patentability corresponding to International Application No. PCT/US2014/042683 dated Dec. 30, 2015.
International Preliminary Report on Patentability corresponding to International Application No. PCT/US2011/066843 dated Jul. 4, 2013.
International Preliminary Report on Patentability Corresponding to International application No. PCT/US2018/021986 dated Sep. 10, 2019.
International Preliminary Report on Patentability corresponding to International application No. PCT/US2018/059152 dated May 14, 2020.
International Search Report and the Written Opinion of the International Searching Authority Corresponding to International Application No. PCT/US2018/040774 dated Sep. 18, 2018.
International Search Report and the Written Opinion of the International Searching Authority corresponding to International application No. PCT/US2018/059152 dated Mar. 6, 2019.
International Search Report and Written Opinion of the International Searching Authority Corresponding to International Patent Application No. PCT/US2020/060581 dated Feb. 11, 2021.
International Search Report corresponding to International Application No. PCT/US2019/037993 dated Oct. 18, 2019.
International Search Report corresponding to International Application No. PCT/US2014/042683 dated Oct. 9, 2014.
International Search Report Corresponding to International application No. PCT/US2018/021986 dated Aug. 1, 2018.
Jackson et al., "Thromboinflammation: challenges of therapeutically targeting coagulation and other host defense mechanisms." Blood, vol. 133, pp. 906-918 (2019).
Jaeschke et al., "Complement activates Kupffer cells and neutrophils during reperfusion after hepatic ischemia." Am. J. Physiol-Gastroint. Liver Physiol., vol. 264, pp. G801-G809 (1993).
Jaimes et al., "Unfractioned heparin for treatment of sepsis: A randomized clinical trial (The HETRASE Study)." Crit. Care Med., vol. 37, pp. 1185-1196 (2009).
Jemth et al., "Oligosaccharide library-based assessment of heparan sulfate 6-0-sulfotransferase substrate specificity," Journal of Biological Chemistry, vol. 278, No. 27, pp. 24371-24376 (Jul. 4, 2003).
Jin, L.; Abrahams, P.; Skinner, R.; Petitou, M.; Pike, R. N.; Carrell, R. W. Proc. Natl. Acad. Sci. 1997, 94, 14683.

Kakkar et al., "Low Molecular Weight Heparin, Therapy With Dalteparin, and Survival in Advanced Cancer: The Fragmin Advanced Malignancy Outcome Study (FAMOUS)," J. Clin. Oncol., vol. 22, No. 10, pp. 1944-1948 (May 15, 2004).
Kakuta et al., "Heparan sulphate N-sulphotransferase activity: reaction mechanism and substrate recognition," Biochem. Soc. Trans., vol. 31 (pt2), pp. 331-334 (2003).
Kamimura, K.; Rhodes, J. M.; Ueda, R.; McNeely, M.; Shukla, D.; Kimata, K.; Spear, P. G.; Shworak, N. W.; Nakata, H. J. Cell Biol. 2004, 166, 1069.
Kaneko et al., "Coagulation and fibrinolytic profiles and appropriate use of heparin after living-donor liver transplantation." Clin. Transplant. Vol. 19. pp. 804-809 (2005).
Kirschner, K. N.; Yongye, A B.; Tschampel, S. M.; Gonzalez-Outeirino, J.; Daniels, C. R.; Foley, B. L.; Woods, R. J. J. Comput. Chem. 2008, 29, 622.
Kisselev, L., "Polypeptide release factors in prokaryotes and eukaryotes: same function, different structure," Structure, vol. 10, pp. 8-9 (2002).
Kollman, P. A; Massova, I.; Reyes, C.; Kuhn, B.; Hua, S.; Chong, L.; Lee, M.; Lee, T.; Duan, Y.; Wang, W.; Donini, O.; Cieplak, P.; Srinivasan, J.; Case, D. A; Cheatham, T. E. r. Acc. Chem. Res. 2000, 33, 889.
Konishi et al., "Hepatic ischemia/reperfusion: mechanisms of tissue injury, repair, and regeneration." Gene Expr., vol. 17, pp. 277-287 (2017).
Kopec et al., "Fibrin(ogen) drives repair after acetaminophen-induced liver injury via leukocyte aMb2 integrin-dependent upregulation of Mmp12." J. Hepatol. vol. 66, pp. 787-797 (2017).
Kreimann, M.; Brandt, S.; Krauel, K.; Block, S.; Helm, C.; Weitschies, W.; Greinacher, A.; Delcea, M. Blood 2014, in press.
Kreuger et al., Interactions between heparan sulfate and proteins: the concept of specificity, J. Cell Biol., vol. 174, No. 3, pp. 323-327 (Jul. 31, 2006).
Krummenacher et al., "The First Immunoglobulin-Like Domain of HveC Is Sufficient to Bind Herpes Simplex Virus gD with Full Affinity, While the Third Domain Is Involved in Oligomerization of HveC," J. Virol., vol. 73, pp. 8127-8137 (Oct. 1999).
Kuberan et al., "Enzymatic synthesis of antithrombin III-binding heparan sulfate pentasaccharide," Nature Biotechnology, vol. 21, No. 11, 1343-1346 (Nov. 2003).
Kuberan et al., "Rapid Two-Step Synthesis of Mitrin from Heparosan: A Replacement for Heparin," J. Am. Chem. Soc., vol. 125, pp. 12424-12425 (2003).
Kuberan et al., The Journal of Biological Chemistry, "Chemoenzymatic Synthesis of Classic and Non-classical Anticoagulant Heparan Sulfate Polysaccharides", 2003, vol. 278, No. 52, pp. 52613-52621 (Year: 2003).
Kubes et al., "Sterile inflammation in the liver." Gastroenterology, vol. 143, pp. 1158-1172 (2012).
Kyte & Doolittle (1982) A Simple Method for Displaying the Hydropathic Character of a Protein. J. Mol Biol, 157: 105-132.
Langdown, J.; Belzar, K. J.; Savory, W. J.; Baglin, T. P.; Huntington, J. A. J. Mo/. Biol. 2009, 386, 1278.
Laurent et al., "The Molecular-Weight-Dependence of the Anti-Coagulant Activity of Heparin," Biochem. J., vol. 175, pp. 691-701 (1978).
Ledin et al., "Heparan Sulfate Structure in Mice with Genetically Modified Heparan Sulfate Production," J. Biol. Chem., vol. 279, No. 41, pp. 42732-42741 (2004).
Lee, "Acetaminophen toxicity: changing perceptions on a social/medical issue." Hepatology, vol. 46, pp. 966-970 (2007).
Lee, M.K., and Lander, A.D., (1991) Proc. Natl. Acad. Sci. USA 88, 2768-2772.
Li et al., "Biosynthesis of Heparin/Heparan Sulfate cDNA Cloning and Expression of D-Glucuronyl C5-Epimerase From Bovine Lung," J. Biol. Chem., vol. 272, No. 4, pp. 28158-28163 (Oct. 31, 1997).
Li et al., "Enzymatic synthesis of homogenous chondroitin sulfate e oligosaccharides," Abstract of Glycobiol., vol. 28(12) (2018) [Abstract].
Li J, Su W, and Liu J. "Enzymatic synthesis of homogeneous chondroitin sulfate oligosaccharides." Angew Chem Int Ed. 2017;56:11784-7.

(56) References Cited

OTHER PUBLICATIONS

Liliensiek et al., "Receptor for advanced glycation end products (RAGE) regulates sepsis but not the adaptive immune response." J. Clin. Invest. vol. 113, pp. 1641-1650 (2004).

Lin et al., "Colorimetric Determination of the Purity of 39-Phospho Adenosine 59-Phosphosulfate and Natural Abundance of 39-Phospho Adenosine 59-Phosphate at Picomole Quantities," Anal. Biochem., vol. 264, pp. 111-117 (1998).

Lin et al., "Enzymatic Synthesis and Regeneration of 3'-Phosphoadenosine 5'Phosphosulfate (PAPS) for Regioselective Sulfation of Oligosaccharides," J. Am. Chem. So., vol. 117, pp. 8031-8032 (1995).

Lindahl et al., "Regulated Diversity of Heparan Sulfate," The Journal of Biological Chemistry, vol. 273, No. 39, pp. 24979-24982 (Sep. 25, 1998).

Lindahl et al., "Generation of "Neoheparin" from E. coli K5 Capsular Polysaccharide," J. Med. Chem., vol. 48, pp. 349-352 (2005).

Lindahl, U.; Backstrom, G.; Thunberg, L.; Leder, I. G. Proc. Natl. Acad. Sci. 1980, 77, 6551.

Linhardt et al., "Production and Chemical Processing of Low Molecular WQeight Heparins," Seminars in Thrombosis and Hemostasis, vol. 25, Suppl.3, pp. 5-16 (1999).

Linhardt, R. J., J. Med. Chem., vol. 46, pp. 2551-2564 (2003).

Liu et al., "Anticoagulant heparan sulfate: structural specificity and biosynthesis," Appl Microbiol Biotechnol., vol. 74, pp. 263-272 (2007).

Liu et al., "Cell Surface Heparan Sulfate and Its Roles in Assisting Viral Infections," Medicinal Research Reviews, vol. 22, No. 1, pp. 1-25 (2002).

Liu et al., "Characterization of a Heparan Sulfate Octasaccharide that Binds to Herpes Simplex Virus Type 1 Glycoprotein D," The Journal of Biological Chemistry, vol. 277, No. 36, pp. 33456-33467 (Sep. 6, 2002).

Liu et al., "Expression of Heparan Sulfate D-Glucosaminyl 3-O-Sulfotransferase Isoforms Reveals Novel Substrate Specificities," The Journal of Biological Chemistry, vol. 274, No. 8, pp. 5185-5192 (Feb. 19, 1999).

Liu et al., "Purification of Heparan Sulfate D-Glucosaminyl 3-O-Sulfotransferase," The Journal of Biological Chemistry, vol. 271, No. 43, pp. 27072-27082 (Oct. 25, 1996).

Liu et al., Chemoenzymatic Design of Heparan Sulfate Oligosaccharides, J Biol Chem, vol. 285, No. 44, pp. 34240-34249 (Oct. 29, 2010).

Liu et al., "Enzymatic Placement of 6-O-Sulfo Groups in Heparan Sulfate," Biochemistry 2011, 50, 4382-4391.

Liu et al., "Lessons learned from the contamination of heparin," Nat. Prod. Rep., vol. 26, pp. 313-321 (2009).

Liu, J. et al., Royal Society of Chemistry, "Chemoenzymatic synthesis of heparan sulfate and heparin", vol. 31, pp. 1676-1685 (Year: 2014).

Loganathan et al., "Structural Variation in the Antithrombin III Binding Site Region and Its Occurrence in Heparin from Different Sources," Biochemistry, vol. 29, pp. 4362-4368 (1990).

Lopin et al., "From Polymer to Size-Defined Oligomers: An Expeditious Route for the Preparation of Chondroitin Oligosaccharides." Angew. Chem. Int. Ed., vol. 45, pp. 2574-2578 (2006).

Lopin-Bon et al., "Stereocontrolled preparation of biotinylated chondroitin sulfate E di-, tetra-, and hexasaccharide conjugates." Carbohydr. Res., vol. 402, pp. 35-43 (2015).

Lu et al., "Innate Immune Regulations and Liver Ischemia-Reperfusion Injury." Trasplantation, vol. 100, pp. 2601-2610 (2016).

Lundbäck et al., "A novel high mobility group box 1 neutralizing chimeric antibody attenuates drug-induced liver injury and postinjury inflammation in mice." Hepatology vol. 64, pp. 1699-1710 (2016).

Ly et al., "The proteoglycan bikunin has a defined sequence." Nat. Chem. Biol., vol. 7, pp. 827-833 (2011).

Maccarana et al., J. Biol. Chem., vol. 268, pp. 23898-23905 (1993).

Macchione et al., "Synthesis of chondroitin sulfate oligosaccharides using N-tetrachlorophthaloyl and N-trifluoroacetyl galactosamine building blocks," European Journal of Organic Chemistry, pp. 3868-3884 (2014).

Mackman, "Triggers, targets and treatments for thrombosis," Nature, vol. 451, No. 21, pp. 914-918 (Feb. 21, 2008).

Mahe, I.; Chidac, J.; Helfer, H.; Nobel, S. J. Thromb. Haemost. 2016, 14, 2107.

Man et al., "Tolerance of the liver to intermittent pringle maneuver in hepatectomy for liver tumors." JAMA Sirgery, vol. 134, pp. 533-539 (1999).

Marcus et al. Anal. Biochem., vol. 107, pp. 296-304 (1980).

Marshall et al., "A review of the effects of manipulation of the cysteine residues of rat aryl sulfotransferase IV," Chem. Biol. Interact., vol. 109, pp. 107-116 (1998).

Marshall et al., "Control of Activity through Oxidative Modification at the Conserved Residue Cys66 of Aryl Sulfotransferase IV," J. Biol. Chem., vol. 272, No. 14, pp. 9153-9160 (Apr. 14, 1997).

Martinez-Gonzalez et al., "New Challenges for a Second-Generation Low-Molecular-Weight Heparin: Focus on Bemiparin," Expert Rev. Cardiovasc. Ther., vol. 8, No. 5, pp. 625-634 (2010).

Mazany et al., "Human chondroitin 6-sulfotransferase: cloning, gene structure, and chromosomal localization," Biochimica et Biophysica Acta, vol. 1407, pp. 92-97 (1998).

McGowan, K. E.; Makari, J.; Diamantouros, A.; Bucci, C.; Rempel, P.; Selby, R.; Geerts, W. Blood 2016, 127, 1954.

Miyachi et al., "Syntheses of chondroitin sulfate tetrasaccharide structures containing 4,6-disulfate patterns and analysis of their interaction with glycosaminoglycan-binding protein." Bioorg. Med. Chem. Lett., vol. 25, pp. 1552-1555 (2015).

Miyata et al., "Persistent cortical plasticity by upregulation of chondroitin 6-sulfation." Nat. Neurosci., vol. 15, pp. 414-422 (2012).

Mizumoto et al., "Molecular interactions between chondroitin-dermatan sulfate and growth factors/receptors/matrix proteins." Curr. Opin. Struct. Biol., vol. 34, pp. 35-42 (2015).

Monneau et al., "The sweet spot: how GAGs help chemokines guide migrating cells." J. Leukoc. Biol. vol. 99, pp. 935-953 (2016).

Moon et al., "Dissecting the substrate recognition of 3-O-suflotransferase for the biosynthesis of anticoagulant heparin," Proceedings of the National Academy of Sciences, vol. 109, No. 14, pp. 5265-5270 ( 2012).

Moon et al., "Structural Analysis of the Sulfotransferase (3-O-Sulfotransferase Isoform 3) Involved in the Biosynthesis of an Entry Receptor for Herpes Simplex Virus 1," J. Biol. Chem., vol. 279, No. 43, pp. 45185-45193 (2004).

Mossanen et al., "Acetaminophen-induced acute liver injury in mice." Lab. Anim. vol. 49, pp. 30-36 (2015).

Mousa, "Drug Discovery and Evaluation: Pharmacological Assays" (ed. Vogel, H.), 393-456 (Springer-Verlag Berlin, Heidelberg, New York (2008).

Mousa, "Heparin and Low-Molecular Weight Heparins in Thrombosis and Beyond," Meth. Mol. Biol., vol. 663, pp. 109-132 (2010).

Mousa, "In Vitro Methods of Evaluating Antithrombotics and Thrombolytics," Meth. Mol. Biol., vol. 663, pp. 1-28 (2010).

Munoz et al., "Enzymatic synthesis of heparin related polysaccharides on sensor chips: Rapid screening of heparin-protein interactions," Biochemical and Biophysical Research Communications, Academic Press Inc., Orlando, FL, US, vol. 339, No. 2, pp. 597-602 (Jan. 13, 2006).

Nadanaka et al., "Characteristic Hexasaccharide Sequences in Octasaccharides Derived from Shark Cartilage Chondroitin Sulfate D with a Neurite Outgrowth Promoting Activity," The Journal of Biological Chemistry, vol. 273(6), pp. 3296-3307 (1998).

Nagano et al., "Chondroitin sulfate protects vascular endothelial cells from toxicities of extracellular histones." Eur. J. Pharmacol., vol. 826, pp. 48-55 (2018).

Nam et al., "Syndecan-1 Limits the Progression of Liver Injury and Promotes Liver Repair in Acetaminophen-Induced Liver Injury in Mice." Hepatology, vol. 66(5), pp. 1601-1615, doi: 10.1002/hep. 29265 (2017).

(56) References Cited

OTHER PUBLICATIONS

Nastuk et al., "Expression Cloning and Characterization of NSIST, a Novel Sulfotransferase Expressed by a Subset of Neurons and Postsynaptic Targets," The Journal of Neuroscience, vol. 18, No. 18, pp. 7167-7177 (Sep. 15, 1998).
Needleman et al., "A General Method Applicable to the Search for Similarities in the Amino Acid Sequence of Two Proteins," J. Mol. Biol., vol. 48, pp. 443-453 (1970).
Nicola et al., Structure-Function Analysis of Soluble Forms of Herpes Simplex Virus Glycoprotein D., J. Virol., vol. 70, No. 6, pp. 3815-3822 (1996).
Noti et al., "Chemical Approaches to Define the Review Structure-Activity Relationship of Heparin-like Glycosaminoglycans," Chemistry & Biology, vol. 12, pp. 731-756 (Jul. 2005).
Notice of Allowance and Interview Summary corresponding to U.S. Appl. No. 17/254,145 dated Jan. 30, 2023.
Notice of Allowance and Interview Summary corresponding to U.S. Appl. No. 14/898,865 dated Dec. 15, 2017.
Notice of Allowance corresponding to U.S. Appl. No. 17/254,145 dated Dec. 8, 2022.
Notice of Allowance corresponding to U.S. Appl. No. 16/492,858 dated Sep. 12, 2022.
Notice of Allowance corresponding to U.S. Appl. No. 16/492,858 dated Feb. 10, 2023.
Notice of Allowance corresponding to U.S. Appl. No. 13/996,930 dated Aug. 11, 2021.
Notice of Issuance corresponding to Chinese Patent Application No. 201480044429.9 dated May 18, 2021.
Notice of Publication Corresponding to European Patent Application. No. 19822610.2 dated Mar. 31, 2021.
Notice of Publication Corresponding to European Patent application No. 18764628.6 dated Nov. 20, 2019.
Notice of Publication Corresponding to European Patent Application No. 18873131.9 dated Jul. 15, 2020.
Notice of Publication of Application Corresponding to U.S. Appl. No. 17/254,145 dated Aug. 27, 2021.
Notification Concerning of Transmittal of International Preliminary Report on Patentability for International Application No. PCT/US2006/018778 (Nov. 14, 2007).
Notification of Transmittal of the International Search Report and the Written Opinion of the International Searching Authority, or the Declaration for International Application No. PCT/US06/18778 (Feb. 21, 2007).
Notification of Transmittal of the International Search Report and the Written Opinion of the International Searching Authority, or the Declaration corresponding to International Application No. PCT/US2008/008945 (Feb. 20, 2009).
Notification of Transmittal of the International Search Report and the Written Opinion of the International Searching Authority, or the Declaration corresponding to International Application No. PCT/US2011/066843 dated Aug. 22, 2012.
Oduah et al., "Heparin: Past, present, and future." Pharmaceuticals (Basel), vol. 9, Article No. 38 (2016).
Office Action (Decision of Rejection) corresponding to Chinese Patent Application No. 20180020095.X dated Dec. 1, 2022.
Office Action (Notice of Reasons for Rejection) corresponding to Japanese Patent Application No. 2020-570916 dated Jun. 20, 2023.
Office Action (Restriction Requirement) corresponding to U.S. Appl. No. 17/254,145 dated Nov. 26, 2021.
Office Action (Restriction Requirement) corresponding to U.S. Appl. No. 16/761,159 dated Jun. 10, 2022.
Office Action (Restriction Requirement) corresponding to U.S. Appl. No. 16/492,858 dated Jun. 30, 2021.
Office Action corresponding to Chinese Patent Application No. 201880020095.X dated Jun. 8, 2022.
Office Action corresponding to Chinese Patent Application No. 201480044429.9 dated Aug. 30, 2018.
Office Action corresponding to Chinese Patent Application No. 201480044429.9 dated Apr. 9, 2019.
Office Action corresponding to Chinese Patent Application No. 201480044429.9 dated Mar. 3, 2020.
Office Action corresponding to Chinese Patent Application No. 201880020095.X dated Sep. 22, 2021.
Office Action corresponding to Chinese Patent Application No. 2018800850125 dated Jan. 20, 2023.
Office Action corresponding to Chinese Patent Application No. 201880020095.X dated Apr. 18, 2023.
Office Action corresponding to Chinese Patent Application No. 2019800446973 dated Jul. 7, 2023.
Office Action corresponding to Chinese patent Application No. 202310342719.2 dated May 8, 2023. .
Office Action corresponding to Chinese Patent Application No. 202080092892 dated Jun. 21, 2023.
Office Action corresponding to European Patent Application No. 11849994.6 dated May 24, 2018.
Office Action corresponding to European Patent Application No. 11849994.6 dated Jan. 22, 2020.
Office Action corresponding to European Patent Application No. 14812890.3 dated Jun. 23, 2020.
Office Action corresponding to European Patent Application No. 18873131.9-1112 dated Aug. 14, 2023.
Office Action corresponding to Japanese Patent Application No. 2019-549419 dated Dec. 23, 2022.
Office Action corresponding to Japanese Patent Application No. 2016-521505 dated Jul. 19, 2018.
Office Action corresponding to Japanese Patent Application No. 2016-521505 dated Jun. 21, 2019.
Office Action corresponding to Japanese Patent Application No. 2019-549419 dated Mar. 22, 2022.
Office Action corresponding to Japanese Patent Application No. 2020-544568 dated Jan. 10. 2023.
Office Action corresponding to U.S. Appl. No. 12/178,434 dated Oct. 28, 2011.
Office Action corresponding to U.S. Appl. No. 12/178,434 dated Apr. 19, 2011.
Office Action corresponding to U.S. Appl. No. 12/178,434 dated Jan. 26, 2011.
Office Action corresponding to U.S. Appl. No. 16/492,858 dated Jan. 13, 2022.
Office Action corresponding to U.S. Appl. No. 16/761,159 dated Jan. 11, 2023.
Office Action corresponding to U.S. Appl. No. 17/254,145 dated Feb. 16, 2022.
Office Action corresponding to U.S. Appl. No. 13/996,930 dated Oct. 8, 2015.
Office Action corresponding to U.S. Appl. No. 13/996,930 dated May 26, 2016.
Office Action corresponding to U.S. Appl. No. 13/996,930 dated Dec. 21, 2017.
Office Action corresponding to U.S. Appl. No. 13/996,930 dated Jul. 30, 2018.
Office Action corresponding to U.S. Appl. No. 13/996,930 dated Nov. 22, 2019.
Official Action corresponding to U.S. Appl. No. 11/920,319 dated Apr. 28, 2010.
Official Action corresponding to U.S. Appl. No. 14/898,865 dated Mar. 23, 2017.
Oliveira et al., "Neutrophils: a cornerstone of liver ischemia and reperfusion injury." Lab. Invest., vol. 98, pp. 51-62 (2018).
Ong et al., "Expression Cloning of a Human Sulfotransferase that Directs the Synthesis of the HNK-1 Glycan on the Neural Cell Adhesion Molecule and Glycolipids," The Journal of Biological Chemistry, vol. 273, No. 9, pp. 5190-5195 (Feb. 27, 1998).
Onufriev, A; Bashford, D.; Case, D. A Proteins 2004, 55, 383.
Ornitz et al., "Receptor Specificity of the Fibroblast Growth Factor Family," J. Biol. Chem., vol. 271, No. 25, pp. 15292-15297 (1996).
Ouyang et al., "Molecular Cloning and Expression of Human and Mouse Tyrosylprotein Sulfotransferase-2 and a Tyrosylprotein Sulfotransferase Homologue in Caenorhabditis elegans," The Journal of Biological Chemistry, vol. 273, No. 38, pp. 24770-24774 (Sep. 18, 1998).

(56) References Cited

OTHER PUBLICATIONS

Ozawa et al., "Nucleotide sequence of a full-length cDNA (PST-1) for aryl sulfotransferase from rat liver," Nucleic Acids Res., vol. 18, No. 13, p. 4001 (1990).

Park et al., "Cell surface heparan sulfate proteoglycans: selective regulators of ligand-receptor encounters." J. Biol. Chem. vol. 275, pp. 29923-29926 (2000).

Patel, V. N.; Lombaert, I. M.A.; Cowherd, S. N.; Shworak, N.; Xu, Y.; Liu, J.; Hoffman, M. P. Developmental Cell 2014, 29, 662.

Pempe, et al., "Probing Structural Selectivity of Synthetic Heparin Binding to Stabilin Protein Receptors," Journal of Biol. Chem., vol. 287, No. 25, pp. 20774-20783 (Jun. 15, 2012).

Petitou et al., "A Synthetic Antithrombin III Binding Pentasaccharide Is Now a Drug! What Comes Next?" Angew. Chem. Int. Ed., vol. 43, pp. 3118-3133 (2004).

Petitou et al., "Synthesis of thrombin-inhibiting heparin mimetics without side effects." Nature, vol. 398, pp. 417-422 (Apr. 1, 1999).

Pettersen, E. F.; Goddard, T. D.; Huang, C. C.; Couch, G. S.; Greenblatt, D. M.; Meng, E. C.; Ferrin, T. E. J. Comp. Chem. 2004, 25, 1605.

Pierce et al., "Inflammatory response to trauma: implications for coagulation and resuscitation." Curr. Opin. Anesthesio., vol. 27, pp. 246-252 (2014).

Pinhal et al., "Enzyme interactions in heparan sulfate biosynthesis: Uronosyl 5-epimerase and 2-O-sulfotransferase interact in vivo.," Proc. Natl. Acad. Sci. U. S. A., vol. 98, No. 23, p. 12984-12989 (Nov. 6, 2001).

Proudfoot et al., "Glycosaminoglycan binding and oligomerization are essential for the in vivo activity of certain chemokines." Proc. Natl. Acad. Sci. USA vol. 100, pp. 1885-1890 (2003).

Pulsipher et al., Directing Neuronal Signaling through Cell-Surface Glycan Engineering.º J. Am. Chem. Soc., vol. 136, pp. 6794-6797 (2014).

Pye et al., "Heparan Sulfate Oligosaccharides Require 6-O-Sulfation for Promotion of Basic Fibroblast Growth Factor Mitogenic Activity," J. Biol. Chem., vol. 273, No. 36, pp. 22936-22942 (Sep. 4, 1998).

Raman, R.; Venkataraman, G.; Ernst, S.; Sasisekharan, R. Proc. Natl. Acad. Sci. 2003, 100, 2357.

Razi et al., "Structural and functional properties of heparin analogues obtained by chemical sulphation of *Escherichia coli* K5 capsular polysaccharide," Biochem. J., vol. 389, pp. 465-472 (1995).

Reizes et al., "Transgenic Expression of Syndecan-1 Uncovers a Physiological Control of Feeding Behavior by Syndecan-3," Cell, vol. 106, pp. 105-116 (Jul. 13, 2001).

Rohrmann et al., "Two N-acetylgalactosaminyltransferase are involved in the biosynthesis of chondroitin sulfate," European Journal of Biochemistry, vol. 148, pp. 463-469 (1985).

Roman-Blas et al., "The combined therapy with chondroitin sulfate plus glucosamine sulfate or chondroitin sulfate plus glucosamine hydrochloride does not improve joint damage in an experimental model of knee osteoarthritis in rabbits." Eur. J. Pharmacol., vol. 794, pp. 8-14 (2017).

Rosenberg et al., "Heparan Sulfate Proteoglycans of the Cardiovascular System Specific Structures Emerge But How Is Synthesis Regulated?" J. Clin. Invest., vol. 99, No. 9, pp. 2062-2070 (May 1997).

Saeki et al., "Molecular Cloning, Expression, and Characterization of a Novel Mouse Liver SULT1B1 Sulfotransferase," J. Biochem., vol. 124, pp. 55-64 (1998).

Sala et al., "UDP-N-trifluoroacetylglucosamine as an alternative substrate in N-acetylglucosaminyltransferase reactions", Carbohydrate Research, vol. 306, pp. 127-136 (1998).

Saribas et al., "Production of N-sulfated 1-38 polysaccharides using yeast-expressed N-deacetylase/N-sulfotransferase-1 (NDST-1)," Glycobiology, vol. 14, pp. 1217-1228 (2004).

Sarris et al., "Inflammatory chemokines direct and restrict leukocyte migration within live tissues as glycan-bound gradients." Curr. Biol. Vol. 22, pp. 2375-2382 (2012).

Sasisekharan et al., "Roles of Heparan-Sulphate Glycosaminoglycans in Cancer," Nat. Rev. Cancer, vol. 2, pp. 521-528 (Jul. 2002).

Sattelle, B. M.; Almond, A. Glycobiology 2011, 21, 1651.

Sattelle, B. M.; Hansen, S. U.; Gardiner, J. M.; Almond, A. J Am Chem Soc 2010, 132, 13132.

Schroeder et al., "Protamine neutralization of low molecular weight heparins and their oligosaccharide components," Anal Bioanal Chem, vol. 399, pp. 763-771 (2011).

Schwartz et al., "Virogenic BrdU and BrdU-sensitive DNA sequences are disproportionately concentrated in the template-active chromatin of rat embryo cells," Nuc Acids Res., vol. 6, No. 2. pp. 745-755 (Feb. 1979).

Schworer, R.; Zubkova, O. V.; Turnbull, J. E.; Tyler, P. C. Chem. Eur. J. 2013, 19, 6817.

Sheng et al., "Influenced of Phenylalanines 77 and 138 on the Stereospecifity of Aryl Sulfotransferase IV." Drug Metabol. Dispos., vol. 32, No. 5, pp. 559-565 (2004).

Sheng et al., "The Dominating Role of N-Deacetylase/N-Sulfotransferase 1 in Forming Domain Structures in Heparan Sulfate," The Journal of Biological Chemistry, vol. 286, No. 22, p. 19768-19776 (Jun. 3, 2011).

Shiori et al., "Sequence determination of synthesized chondroitin sulfate dodecasaccharides." Glycobiology, vol. 26, pp. 592-606 (2016).

Shively et al., "Formation of Anhydrosugars in the Chemical Depolymerization of Heparin," Biochemistry, vol. 15, No. 18, pp. 3932-3942 (1976).

Shriver et al., (2012) "Heparin and Heparan Sulfate: Analyzing Structure and Microheterogeneity," Handb Exp. Pharmacol. (207): pp. 159-176.

Shriver et al., "Glycomics: A Pathway to a Class of New and Improved Therapeutics," Nat. Rev. Drug Discov., vol. 3, pp. 863-873 (Oct. 2004).

Shukla et al., "A Novel Role for 3-O-Sulfated Heparan Sulfate in Herpes Simplex Virus 1 Entry," Cell, vol. 99, pp. 13-22 (Oct. 1, 1999).

Shukla et al., "Herpes viruses and heparan sulfate: an intimate relationship in aid of viral entry," The Journal of Clinical Investigation, vol. 108, No. 4, pp. 503-510 (Aug. 2001).

Shworak et al., " Molecular Cloning and Expression of Mouse and Human cDNAs Encoding Heparan Sulfate D-Glucosaminyl 3-O-Sulfotransferase," The Journal of Biological Chemistry, vol. 272, No. 44, pp. 28008-28019 (1997).

Singh, A; Tessier, M. B.; Pederson, K.; Wang, X.; Venot, A P.; Boons, G.-J.; Prestegard, J. H.; Woods, R. J. Can. J. Chem. 2016, 10.1139/cjc.

Sismey-Ragatz, et al., "Chemoenzymatic Synthesis with Distinc Pasteurella Heparosan Synthases," J. Biol. Chem., vol. 282, No. 39, pp. 28321-28327 (Jul. 11, 2007).

Smeds et al., "Substrate specificities of mouse heparan sulphate glucosaminyl 6-O-sulphotransferases," Biochem. J, vol. 372, pp. 371-380 (2003).

Smith et al., "Comparison of Biosequences," Adv. Appl. Math, vol. 2, pp. 482-489 (1981).

Solera et al., "Chondroitin sulfate tetrasaccharides: synthesis, three-dimensional structure and interaction with midkine." Chemistry, vol. 22, pp. 2356-2369 (2016).

Stabler et al., "Chondroitin sulphate inhibits NF-κB activity induced by interaction of pathogenic and damage associated molecules." Osteoarthritis and Cartilage, vol. 25, pp. 166-174 (2017).

STN record for Chen et al., dissertation, "Towards de novo synthesis of structure-defined oligosaccharides with heparan sulfate u biosynthetic enzymes", entered into STN: Apr. 20, 2009. 1 page.

Sugigura et al., "Molecular dissection of placental malaria protein VAR2CSA interaction with a chemo-enzymatically synthesized chondroitin sulfate library." Glycoconj. J., vol. 33, pp. 985-994 (2016).

Sugigura et al., "Sequential synthesis of chondroitin oligosaccharides by immobilized chondroitin polymerase mutants." Glycoconj. J., vol. 25, pp. 521-530 (2008).

Sugiura et al., "Baculovirus Envelope Protein ODV-E66 Is a Novel Chondroitinase with Distinct Substrate Specificity." J. Biol. Chem., vol. 286, pp. 29026-29034 (2011).

(56) References Cited

OTHER PUBLICATIONS

Sugiura et al., "Construction of a Chondroitin Sulfate Library with Defined Structures and Analysis of Molecular Interactions." J. Biol. Chem., vol. 287, pp. 43390-43400 (2012).
Sundaram, M. et al., "Rational design of low-molecular weight heparins with improved in vivo activity," Proc. Natl. Acad. Sci., vol. 100, No. 2, pp. 651-656 (Jan. 21, 2003).
Supplemental Notice of Allowability and Interview Summary corresponding to U.S. Appl. No. 14/898,865 dated Jan. 12, 2018.
Szajek et al., "The US regulatory and pharmacopeia responses to the global heparin contamination crisis." Nat. Biotechnol. vol. 34, pp. 625-630 (2016).
Tamura et al., "Synthesis of chondroitin sulfate E octasaccharide in a repeating region involving an acetamide auxiliary." Carbohydr. Res., vol. 343, pp. 39-47 (2008).
Tecle, E.; Diaz-Balzac, C. A.; Bulow, H. E. G3 (Bethesda) 2013, 3, 541.
Teng et al., "Molecular functions of syndecan-1 in disease." Matrix Biol., vol. 31, pp. 3-16 (2012).
Thacker, B. E.; Seamen, E.; Lawrence, R.; Parker, M. W.; Xu, Y.; Liu, J.; Vander, K. C. W.; Eska, J. D. ACS Chem. Biol. 2016, 11, 971.
Thompson et al., "Clustal W: improving the sensitivity of progressive multiple sequence alignment through sequence weighting, position-specific gap penalties and weight matrix choice," Nucleic Acids Res., vol. 22, No. 22, pp. 4673-4680 (1994).
Tohu et al., Anti-Xa and Anti-IIa Drugs Alter International Normalized Ratio Measurements: Potential Problems in the Monitoring of Oral Anticoagulants Clin. Appl. Thrombos Hemostas, vol. 10, pp. 301-309 (2004).
Tsau, C.; Ito, M.; Gromova, A.; Hoffman, M. P.; Meech, R.; Makarenkova, H. P. Development 2011, 138, 3307.
Tsung et al., "HMGB1 release induced by liver ischemia involves Toll-like receptor 4-dependent reactive oxygen species production and calcium-mediated signaling." J. Exp. Med., vol. 204, pp. 2913-2923 (2007).
Tsung et al., "The nuclear factor HMGB1 mediates hepatic injury after murine liver ischemia-reperfusion." J. Exp. Med., vol. 201, pp. 1135-1143 (2005).
Uchimura et al., "Molecular Cloning and Characterization of an N-Acetylglucosamine-6-O-sulfotransferase," The Journal of Biological Chemistry, vol. 273, No. 35, pp. 22577-22583 (Aug. 28, 1998).
Vann et al., "The Structure of the Capsular Polysaccharide (K5 Antigen) of Urinary-Tract-Infective *Escherichia coli* 010 : K5 : H4 A Polymer Similar to Desulfo-Heparin," Eur. J. Biochem, vol. 116, pp. 359-364 (1981).
Venereau et al., "HMGB1 as biomarker and drug target." Pharmacol. Res. Vol. 111, pp. 534-544 (2016).
Wang et al., "*E. coli* K5 fermentation and the Preparation of Heparosan, a Bioengineered Heparin Precursor," Biotechnol. Bioeng, vol. 107, No. 7, pp. 968-977 (Dec. 15, 2010).
Wang et al., "Edothelial heparan sulfate deficiency impairs L-selectin- and chemokine-mediated neutrophil trafficking during inflammatory responses." Nat. Immunol. vol. 6, pp. 902-910 (2005).
Weber et al., "Renal dysfunction in liver transplant recipients: Evaluation of the critical issues." Liver Transplant., vol. 18, pp. 1290-1301 (2012).
Weitz et al., "Beyond heparin and warfarin: the new generation of anticoagulants," Expert Opin. Investig. Drugs, vol. 16, No. 3, pp. 271-282 (2007).
Weitz, "Potential of new anticoagulants in patients with cancer," Thromb. Res., vol. 125 (Suppl 2), pp. S30-S35 (2010).
Wildhagen et al., "Nonanticoagulant heparin prevents histone-mediated cytotoxicity in vitro and improves survival in sepsis." Blood vol. 123, pp. 1098-1101 (2014).
Willis et al., "Examination of the Kinetics of Herpes Simplex Virus Glycoprotein D Binding to the Herpesvirus Entry Mediator, Using Surface Plasmon Resonance," J. Virol., vol. 72, pp. 5938-5947 (Jul. 1998).
Wishart et al., "A single mutation converts a novel phosphotyosine binding domain into a dual-specificity phosphatase," J. Biol. Chem., vol. 270, No. 45, pp. 26782-26785 (1995).
Witkowski et al., "Conversion of b-ketoacyl synthase to a Malonyl Decarboxylase by replacement of the active cysteine with glutamine," Biochemistry, vol. 38, pp. 11643-11650 (1999).
Written Opinion corresponding to International Application No. PCT/US2019/037993 dated Oct. 18, 2019.
Written Opinion of the International Searching Authority Corresponding to International Application No. PCT/US 2018/021986 dated Aug. 1, 2018.
WuDunn et al., "Initial interaction of herpes simplex virus with cells is binding to heparan sulfate," J. Virol., vol. 63, No. 1, pp. 52-58 (1989).
Xia et al., "Heparan Sulfate 3-O-Sulfotransferase Isoform 5 Generates Both an Antithrombin-binding Site and an Entry Receptor for Herpes Simplex Virus, Type 1," J. Biol. Chem., vol. 277, No. 40, pp. 37912-37919 (2002).
Xu et al., "Characterization of heparan sulphate 3-O-sulphotransferase isoform 6 and its role in assisting the entry of herpes simplex virus type 1," Biochem. J. Vol. 385, pp. 451-459 (2005).
Xu et al., Chemoenzymatic Synthesis of Homogeneous Ultralow Molecular Weight Heparins, Science, vol. 334, pp. 498-501 (Oct. 2011).
Xu et al., "Heparan sulfate is essential for high mobility group protein 1 (HMGB1) signaling by the receptor for advanced glycation end products (RAGE)." J. Biol. Chem. vol. 286, pp. 41736-41744 (2011).
Xu et al., "Homogeneous low-molecular-weight heparins with reversible anticoagulant activity." Nat. Chem. Biol. vol. 10, pp. 248-250 (2014).
Xu et al., Synthetic oligosaccharides can replace animal-sourced low-molecular weight heparins Sci. Transl. Med. vol. 9, eaan5954 (2017).
Xu J, Zhang X, Monestier M, Esmon NL, and Esmon CT. Extracellular histones are mediators of death through TLR2 and TLR4 in mouse fatal liver injury. J Immunol. 2011; 187:2626-31.
Xu J. Zhang X, Pelayo R, Monestier M, Ammollo CT, Semeraro F, et al. Extracellular histones are major mediators of death in sepsis. Nat Med. 2009;15:1318-21.
Xu, D. et al., "Engineering sulfotransferases to modify heparan sulfate," Nat Chem Biol, vol. 4, No. 3. pp. 200-202 (Mar. 2008).
Xu, D.; Esko, "Demystifying Heparan Sulfate-Protein Interactions," J. Annu Rev Biochem. 2014, 83, 129.
Xu, D.; Olson, J.; Cole, J. N.; van Wijk, X. M.; Brinkmann, V.; Zychlinsky, A.; Nizet, V.; Eska, J. D.; Chang, Y. C. Infect. Immun. 2015, 83, 3648.
Xu, et al., "Homogeneous low-molecular-weight heparins with reversible anticoagulant activity," Nat Chem Biol., vol. 10, pp. 248-252 (2014).
Xue et al., "Impact of donor binding on polymerization catalyzed by KfoC by regulating the affinity of enzyme for acceptor." Biochim. Biophys. Acta, vol. 1860, pp. 844-855 (2016).
Yang et al. Effects of 3' -phosphoadenosine 5'-phosphate on the activity and folding of phenol sulfotransferase. Chem.- Biol. Interact. 109: 129-135 (1998).
Yang et al., "An Approach to Synthesize Chondroitin Sulfate-E (CS-E) Oligosaccharide Precursors." J. Organic Chem., vol. 83, pp. 5897-5908 (2018).
Yang et al., "Middle region of the Borrelia burgdorferi surface-located protein 1 (Lmp1) interacts with host chondroitin-6-sulfate and independently facilitates infection." Cell Microbiology, vol. 18, 97-110 (2016).
Yang et al., "Two Phenol Sulfotransferase Species from One cDNA: Nature of the Differences," Protein Expression Purif, vol. 8, pp. 423-429 (1996).
Yang, "Inflammation plays a dual role in acetaminophen hepatotoxicity," Translational Medicine Journal, vol. 5, No. 3, pp. 129-133 (Jun. 2016).
Yang, J.; Hsieh, P.; Liu, X.; Zhou, W.; Zhang, X.; Zhao, J.; Xu, Y.; Zhang, F.; Linhardt, R. J.; Liu, J. Chem Comm 2017, 53, 1743.

(56) References Cited

OTHER PUBLICATIONS

Yang, Z.; et al., "UCSF Chimera, Modeller, and IMP: an Integrated Modeling System," J. Struct. Biol. 2012, 179, 269.

Yoshinari et al., "Molecular Cloning, Expression, and Enzymatic Characterization of Rabbit Hydroxysteroid Sulfotransferase AST-RB2 (ST2A8)," J. Biochem., vol. 123, pp. 740-746 (1998).

Yu et al., "Highly Efficient Chemoenzymatic Synthesis of Beta1-3-Linked Galactosides," Chemical Communications, vol. 46(40), pp. 7507-7509 (2010).

Yusa et al., "N-Linked Oligosaccharides on Chondroitin 6-Sulfotransferase-1 Are Required for Production of the Active Enzyme, Golgi Localization, and Sulfotransferase Activity toward Keratan Sulfate." J. Biol. Chem., vol. 281, pp. 20393-20403 (2006).

Zhang et al., "6-O-Sulfotransferase-1 Represents a Critical Enzyme in the Anticoagulant Heparan Sulfate Biosynthetic Pathway*," J. Biol. Chem., vol. 276, pp. 42311-42321 (2001).

Zhang et al., "Solution Structures of Chemoenzymatically Synthesized Heparin and Its Precursors," J. Am. Chem. Soc., vol. 130, pp. 12998-13007 (2008).

Zhang et al., "The Effect of Precursor Structures on the Action of Glucosaminyl 3-O-Sulfotransferase-1 and the Biosynthesis of Anticoagulant Heparan Sulfate," J. Biol. Chem., vol. 276, No. 31, pp. 28806-28813 (2001).

Zhao et al. "Enzymatic route to preparative-scale synthesis of UDP-GlcNAc/GalNAc, their analogues and GDP-fucose," Nat. Protoc., vol. 5, No. 4, pp. 636-646 (2010).

Zhou et al. "Expression of heparin sulfate sulfotransferases in Kluyveromyces lactis and preparation of 3'-phsphoadenosie-5'-phosphosulfate," Glycobiology, vol. 21, No. 6, pp. 771-780 (2011).

Zitvogel et al., "Decoding cell death signals in inflammation and immunity." Cell, vol. 140, pp. 798-804 (2010).

Zong, C.; Huang, R.; Condac, E.; Chiu, Y.; Xiao, W.; Li, Z. Q.; Lu, W.; Ishihara, M.; Wang, S.; Ramiah, A.; Stickney, M.; Azadi, P.; Amster, I. J.; Moremen, K. W.; Wang, L.; Sharp, J. S.; Boons, G.-J. J. Am. Chem. Soc. 2016, 138, 13059.

Communication of the extended European Search report corresponding to European Patent Application No. 20887629 dated Oct. 27, 2023.

Office Action corresponding to European Patent Application No. 18764628.6 dated Nov. 16, 2023.

Office Action Corresponding to Japanese Patent Application serial No. 2020-544568 dated Sep. 26, 2023.

Iba et al., "Danaparoid sodium attenuates the increase in inflammatory cytokines and preserves organ function in endotoxemic rats," Critical Care, vol. 12, Article No. R86 (7 pages) (2008).

Office Action (Notice of Reasons for Rejection) corresponding to Japanese Patent Application No. 2020-570916 dated Jan. 16, 2024.

* cited by examiner

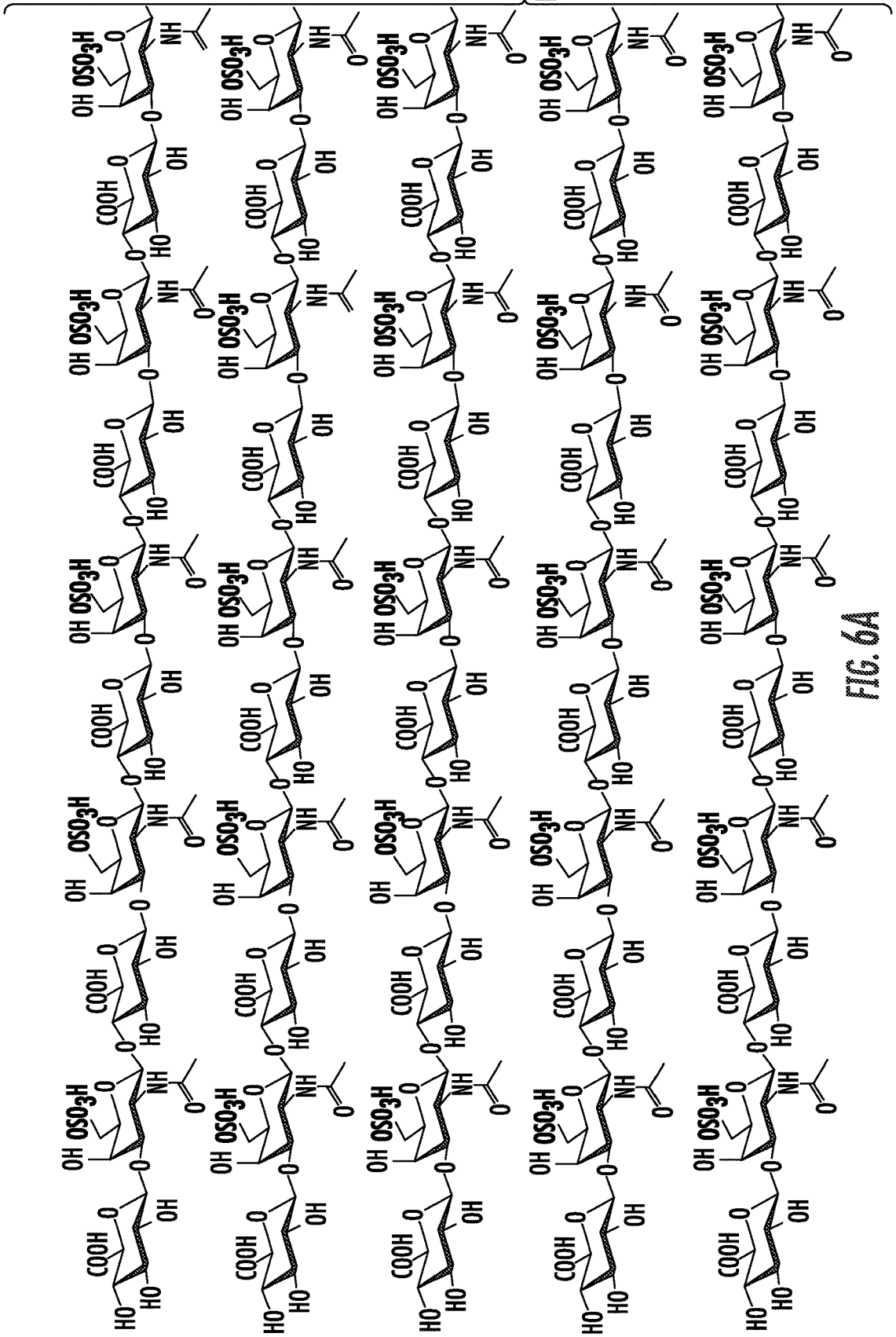

ENZYMATIC SYNTHESIS OF HOMOGENEOUS CHONDROITIN SULFATE OLIGOSACCHARIDES

CROSS-REFERENCE TO RELATED APPLICATIONS

This application is a 35 U.S.C. Section 371 national phase application of PCT International Application Serial No. PCT/US2018/040774, filed Jul. 3, 2018, which claims benefit of U.S. Provisional Patent Application Ser. No. 62/528,243, filed Jul. 3, 2017, herein incorporated by reference in its entirety.

GRANT STATEMENT

This invention was made with government support under Grant Numbers GM102137 and HL094463 awarded by the National Institutes of Health. The government has certain rights in the invention.

TECHNICAL FIELD

The subject matter disclosed herein relates generally to synthesis of chondroitin sulfate oligosaccharides. More particularly, the subject matter disclosed herein relates to methods of enzymatic synthesis of homogenous chondroitin sulfate oligosaccharides, and homogenous chondroitin sulfate oligosaccharides products thereof.

BACKGROUND

Chondroitin sulfates (CS) are sulfated polysaccharides and widely present on the mammalian cell surface and in the extracellular matrix. CS is known to be involved in cancer metastasis[1], parasitic infections[2-3] and neuron growth inhibition after injury[4-6]. The sulfation patterns in CS dictate the binding affinity to the protein targets to manifest the selectivity in biological functions[7]. A 6-O-sulfated N-acetyl galactosamine (GalNAc6S) containing CS facilitates the infection of B. burgdorferi to cause lyme disease[8], and 4-O-sulfated N-acetyl galactosamine (GalNAc4S) involves in P. falciparum infection to cause malaria[2]. A domain containing 4,6 disulfated N-acetyl galactosamine (GalNAc4S6S) residues is proved to be necessary to direct neuronal signaling and inhibit axon growth[6, 9]. CS in conjunction with glucosamine is prescribed as a treatment for osteoarthritis in Asia and Europe and available as a nutraceutical supplement in US; however, the efficacy remains controversial[10-11]. Bikunan, a special form CS, exhibits defined saccharide sequences[12]; however, the CS isolated from natural human or animal tissues are present in a mixture of different sulfated saccharides and sizes. To isolate a polysaccharide with a single sulfated saccharide sequence and defined length is technically demanding. The lack of structurally homogeneous or monodisperse CS is the major roadblock that hinders CS research.

There remains a need for an effective method to synthesize structurally defined CS oligosaccharides to bridge the gap for investigating the structure-activity relationship (SAR). Moreover, there remains a need for the development of methods to synthesize homogeneous CS oligosaccharides at an efficiency high enough to support a wide range of biological evaluations.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are methods of synthesizing a synthetic chondroitin sulfate oligosaccharide, comprising providing a chondroitin backbone, and performing at least two of the following enzymatic reaction steps: an elongation step to add a GalNAc residue using a glycosyltransferase from E. coli K4 (KfoC), an elongation step to add a GlcA residue using KfoC, a 6-O-sulfation step using chondroitin sulfate 6-O-sulfotransferase (CS6OST) and sulfate donor 3'-phosphoadenosine 5'-phosphosulfate (PAPS), and a 4-O-sulfation step involving chondroitin sulfate 4-O-sulfotransferase (CS4OST) and PAPS, whereby a synthetic chondroitin sulfate oligosaccharide is synthesized.

In some embodiments, provided herein are synthetic chondroitin sulfate oligosaccharides produced by the disclosed methods. In some embodiments, provided herein are libraries or panels of synthetic chondroitin sulfate oligosaccharides produced by the disclosed methods. In some embodiments, provided herein are synthetic chondroitin sulfate oligosaccharides comprising a 4-O-sulfated and/or 6-O-sulfated chondroitin oligosaccharide having a size ranging from a 3-mer to a 15-mer. In some embodiments, provided herein are synthetic chondroitin sulfate oligosaccharides comprising are selected from chondroitin sulfate A (CS-A), chondroitin sulfate C (CS-C), chondroitin sulfate D (CS-D) and chondroitin sulfate E (CS-E).

Accordingly, it is an object of the presently disclosed subject matter to provide synthetic chondroitin sulfate oligosaccharides and methods for synthesizing synthetic chondroitin sulfate oligosaccharides.

This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Drawings and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIGS. 6A and 6B are schematic illustrations of the full chemical structures of exemplary CS-C compounds;

DETAILED DESCRIPTION

Figure 1:
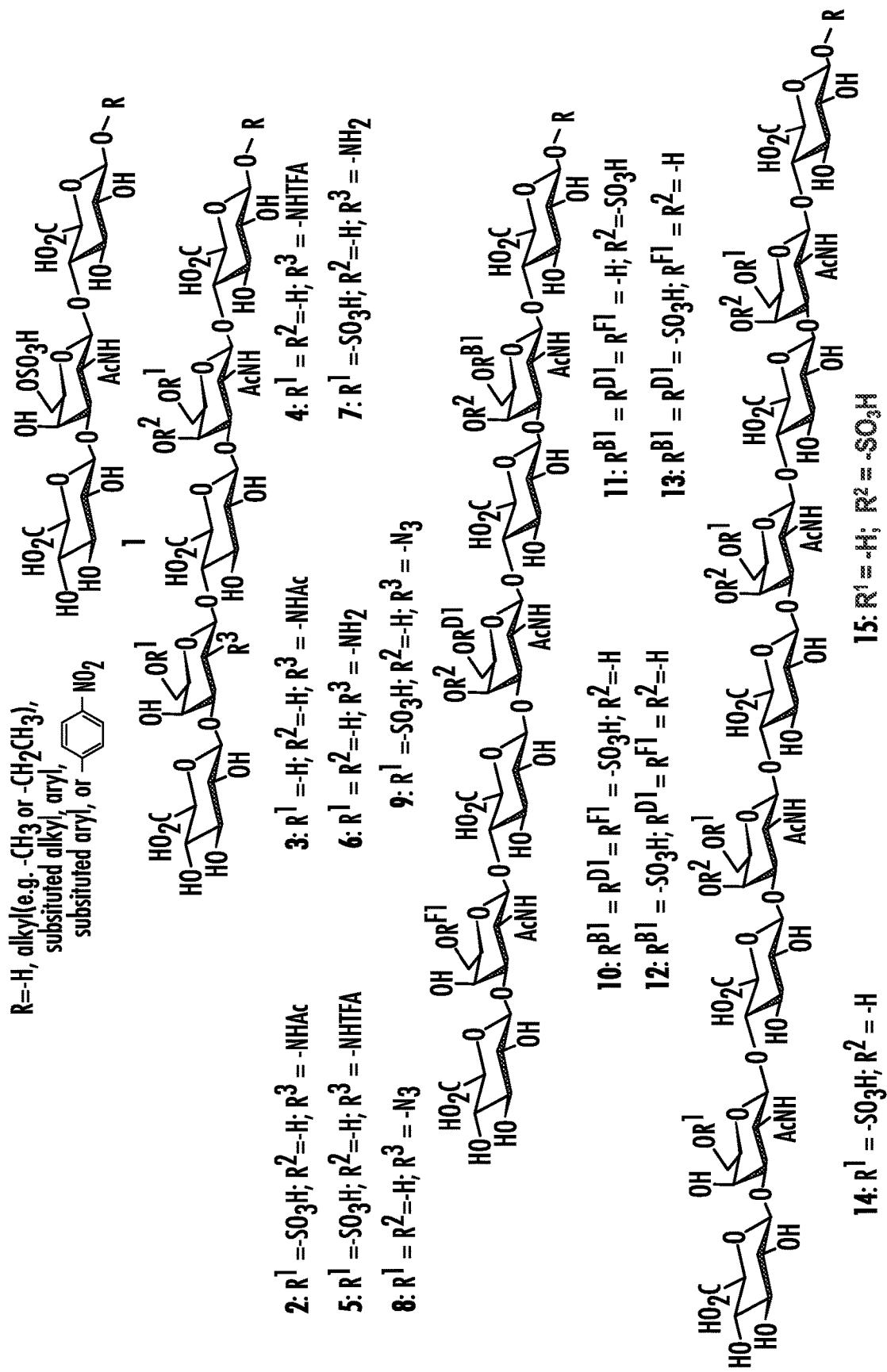
FIG. 1 is a schematic illustration of fifteen exemplary CS compounds synthesized according to the presently disclosed methods.

The presently disclosed subject matter now will be described more fully hereinafter, in which some, but not all embodiments of the presently disclosed subject matter are described. Indeed, the disclosed subject matter can be embodied in many different forms and should not be construed as limited to the embodiments set forth herein; rather, these embodiments are provided so that this disclosure will satisfy applicable legal requirements.

Chondroitin sulfate (CS) is a sulfated polysaccharide that plays essential physiological roles. Disclosed herein are novel enzyme-based methods for synthesizing CS compounds and libraries of CS, including for example a library of CS oligosaccharides comprising a plurality of different CS oligosaccharides ranging from 5-mers to 19-mers. The exemplary library of CS disclosed herein includes 4-O-sulfated and 6-O-sulfated oligosaccharides with the size ranging from trisaccharide to nonasaccharide. Also disclosed herein is the synthesis of unnatural 6-O-sulfated CS pentasaccharides containing either a 6-O-sulfo 2-azido galactosamine or a 6-O-sulfo galactosamine residue. As disclosed herein, the availability of structurally defined CS oligosaccharides, based on the methods and systems disclosed herein, offers a novel approach to investigate the biological functions of CS. In some embodiments, an unnatural CS can be any CS compound where the NHAc has been changed to another moiety, such as an azide or trifluoro, for example. Moreover, a natural CS can be any CS compound that includes a N-acetylgalactosamine (GalNAc). Thus, in some embodiments any CS compound where GalNAc has been modified, changed or removed can be considered unnatural.

To isolate a polysaccharide with a single sulfated saccharide sequence and defined length is technically demanding. The lack of structurally homogeneous or monodisperse CS is a major roadblock that hinders CS research. Thus, until the present disclosure there remained a need for an effective method to synthesize structurally defined CS oligosaccharides to bridge the gap for investigating the structure-activity relationship (SAR). Moreover, the instant disclosure fills a void for methods to synthesize homogeneous CS oligosaccharides at an efficiency high enough to support a wide range of biological evaluations.

Chondroitin sulfates are sulfated polysaccharides and widely present on the mammalian cell surface and in the extracellular matrix. The sulfation patterns in CS dictate the binding affinity to the protein targets to manifest the selectivity in biological functions. For example, a 6-O-sulfated N-acetyl galactosamine (GalNAc6S) containing CS can facilitate the infection of B. burgdorferi to cause lyme disease[8], and 4-O-sulfated N-acetyl galactosamine (GalNAc4S) can be involved in P. falciparum infection to cause malaria[2].

Chondroitin sulfates contain the repeating disaccharide unit of β1→3-linked glucuronic acid (GlcA) and N-acetylgalactosamine (GalNAc) disaccharide, →4)GlcAβ(1→3) GalNAcβ(1→. Both GlcA and GalNAc residues carry sulfo groups, giving rise to different types of CS. Chondroitin sulfate A (CS-A) contains 4-O-sulfated GalNAc (GalNAc4S) residues, chondroitin sulfate C (CS-C) contains 6-O-sulfated GalNAc (GalNAc6S), chondroitin sulfate D (CS-D) contains 2-O-sulfated GlcA and chondroitin sulfate E (CS-E) contains 4,6-O-disulfated GalNAc. Specialized CS sulfotransferases, including 4-O-sulfotransferase (CS4OST), 6-O-sulfotransferase (CS6OST), 2-O-sulfotransferase and GalNAc4S-6-O-sulfotransferase, participate in the biosynthesis of CS.

Unlike chemical synthesis of CS oligosaccharides, provided herein are CS biosynthetic enzymes and methods of using the same to synthesize CS oligosaccharides at a rate, cost and efficiency never before seen. Until the instant disclosure, enzymatic methods, systems and procedure have clearly been unable to prepare homogeneous CS oligosaccharides at an efficiency sufficient to support a wide range of biological evaluations.

A plurality of CS oligosaccharides, including 15 CS oligosaccharides up to 9-mer, were synthesized using the disclosed methods at the scale of about 4 to about 30 mg (see, e.g., FIG. 1 and Table 1). Even longer and/or larger CS oligosaccharides, including up to 19-mer, were also synthesized using the disclosed methods, as shown and illustrated in FIGS. 4, 5A, 5B, 6A, 6B, 7A, 7B, and 8. These CS compounds are exemplary only and not intended to be limited since one of ordinary skill in the art could synthesize any number of CS compounds using the disclosed enzymatic methods, systems and schematics without departing from the scope of the instant disclosure.

In some embodiments, the disclosed methods provide for both the synthesis of nonsulfated chondroitin backbones and sulfations of the backbones to yield the final products. Thus, a CS backbone can in some embodiments be any CS compound without one or more sulfation groups, i.e. a nonsulfated CS compound can be considered a CS backbone. The synthesis of nonsulfated chondroitin was accomplished using a bacterial glycosyltransferase from E. coli K4 strain, known as KfoC. The enzyme transfers both UDP-GalNAc and UDP-GlcA to the acceptor to form chondroitin. The recombinant KfoC was readily obtained through the expression in high yield, offering an effective way to synthesize chondroitin oligosaccharides[22]. However, challenges in preparing oligosaccharides in large quantity and high purity were encountered. First, KfoC displays a promiscuous donor substrate specificity towards N-acetyl hexosamine donors. It transfers a GalNAc residue from UDP-GalNAc to the acceptor, but also transfers an N-acetyl glucosamine (GlcNAc) from UDP-GlcNAc, which is not present in CS[23]. This property raised serious concerns for the purity of the oligosaccharide products if a donor substrate UDP-GalNAc is contaminated with UDP-GlcNAc, causing an incorporation of a GlcNAc residue into the chondroitin backbone. Second, the cost of UDP-GalNAc is high, about $16,000/ mmole from a commercial source. Such price is prohibitively expensive to conduct gram-scale synthesis. To overcome the limitation, UDP-GalNAc was synthesized from GalNAc using two enzymes including N-acetylhexosamine kinase (NAHK) and mammalian GalNAc pyrophosphorylase AGX1. This success eliminated the risk of contamination of UDP-GlcNAc as well as reduced the cost of UDP-GalNAc by about 2500-fold. Using the scheme described in FIGS. 2A and 2B, for example, gram-scale of chondroitin backbone were routinely synthesized to prepare different CS oligosaccharides.

KfoC enzyme is capable of transferring a GalNTFA residue from UDP-GalNTFA, where GalNTFA represented N-trifluoroacetyl galactosamine, into the chondroitin backbone to yield compound 4 (FIG. 2). The introduction of a GalNTFA residue into the backbone offered the flexibility to convert it to a $GalNH_2$ or a $GalN_{AZ}$ residue as demonstrate in the synthesis of compound 6 and 8, respectively. Neither $GalNH_2$ nor $GalN_{AZ}$ residue was reported in CS isolated from natural sources, and these structures have not been synthesized previously. The data provided herein demonstrate that the ability to synthesize structurally diversified chondroitin backbone structures by exploiting the substrate specificity of the enzyme.

4-O-sulfated oligosaccharides were successfully synthesized using CS4OST. In this study, three oligosaccharides, including 4, 11 and 15, were synthesized. Partially 4-O-sulfated products were obtained. Structural analysis of 4, 11, 15 by NMR revealed that the GalNAc residue that is near the nonreducing end was devoid of 4-O-sulfation. The inability of sulfation at the GalNAc near the nonreducing end was attributed to the substrate specificity of CS4OST.

Eight exemplary 6-O-sulfated oligosaccharides were synthesized, including for example CS compounds 1, 2, 5, 7, 9, 10, 13 and 14 (see, e.g. Table 1) using CS6OST. Depending on the positions of 6-O-sulfation, different synthetic schemes were used. Compounds 1, 2, 10 and 14 are fully 6-O-sulfated oligosaccharides ranging from tri-saccharide to nonasaccharide. The synthesis was achieved by incubating the chondroitin backbone (tri- to nona-saccharides) with CS6OST (FIGS. 2A and 2B).

Figure 2A:
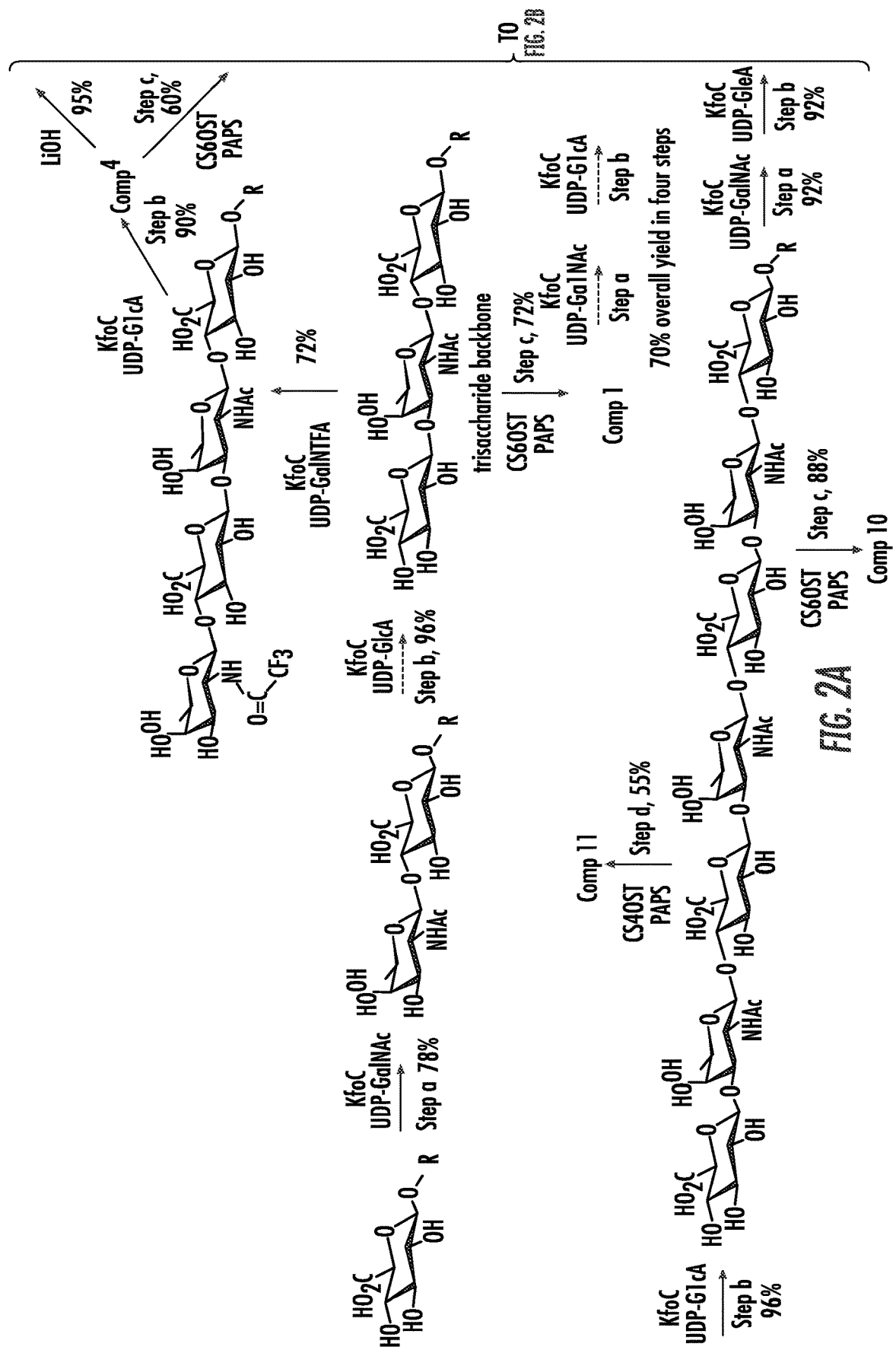
FIGS. 2A and 2B are schematic illustrations of enzymatic method steps and routes for synthesizing CS compounds as disclosed herein.
Figure 2B:
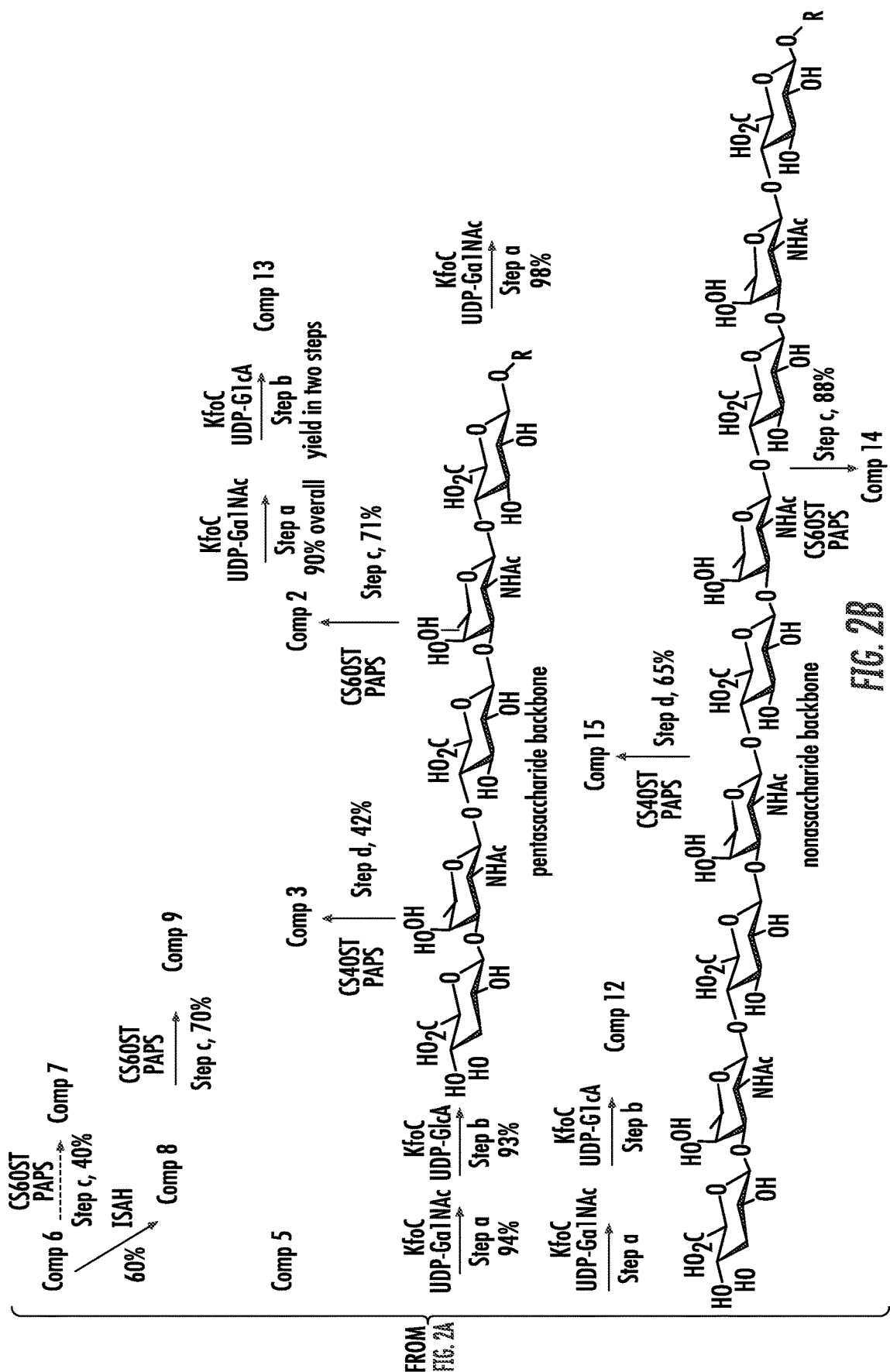

The Synthetic scheme of CS oligosaccharides using enzymes in FIGS. 2A and 2B can in some embodiments comprise the following steps: step a can comprise an elongation step to add a GalNAc residue involving KfoC, a glycosyltransferase from E. coli K4; step b can also comprise an elongation step to add a GlcA residue using KfoC; step c can comprise a 6-O-sulfation step involving chondroitin sulfate 6-O-sulfotransferase (CS6OST) and sulfate donor 3'-phosphoadenosine 5'-phosphosulfate (PAPS); and step d can comprise a 4-O-sulfation step involving chondroitin sulfate 4-O-sulfotransferase (CS4OST) and PAPS. In some embodiments KfoC can also transfer a GalNTFA residue to a trisaccharide backbone to yield a tetrasaccharide. An exemplary yield from each reaction step is indicated in FIGS. 2A and 2B. ISAH represents imidazole-1-sulfonyl azide.

The syntheses of partially 6-O-sulfated heptasaccharides, including compounds 12 and 13, were achieved using different starting 6-O-sulfated oligosaccharides. To synthesize compound 12, a 6-O-sulfated trisaccharide (compound 1) was exposed to elongation reaction using KfoC (FIGS. 2A and 2B). To prepare compound 13, the starting material was compound 2. The rearrangement of the sequence of enzyme modification to achieve partially 6-O-sulfated oligosaccharides demonstrate the flexibility of the enzymatic synthesis to prepare structurally diversified CS-C oligosaccharides.

The chondroitin backbones containing a GalNTFA, $GalNH_2$ or $GalN_{AZ}$ residue were employed to prepare the 6-O-sulfated oligosaccharides, compound 5, 7 and 9 (FIGS. 2A and 2B). The success of synthesis of compound 5, 7, and 9 demonstrated that CS6OST displays the tolerance on the amino substitution of the GalNAc residue. However, the enzyme appears to be very specific towards the chondroitin backbone. Using a heparan hexasaccharide substrate, no reaction was found where the repeating disaccharide unit is β-1,4-linked GlcA and N-acetylated glucosamine (GlcNAc), →4)GlcAβ(1→4) GlcNAcα(1→.

Based on the instant disclosure it has been discovered that at least one desirable factor to synthesize CS-A and CS-C oligosaccharides was to obtain high quality recombinant CS4OST and CS6OST. The enzymes were obtained from insect cells using baculovirus expression approach. In some embodiments it was desirable to remove the viral chondroitinase contamination from enzyme preparations. The chondroitinase degraded chondroitin backbone substrate, leaving no products. The expression of CS6OST in E. coli was unsuccessful, possibly due to the fact that glycosylation is required for the sulfotransferase activity.

TABLE 1

Summary of synthetized CS oligosaccharides up to 9-mer

| Compound | Abbreviated saccharide sequence | Amount (mg) | Purity[1] (%) | Measured Molecular Mass (Da) | Calculated molecular Mass (Da) |
|---|---|---|---|---|---|
| 1 | GlcA-GalNAc6S-GlcA-pNP | 4 | 96% | 774.0 ± 0.6 | 774.6 |
| 2 | GlcA-GalNAc6S-GlcA-GalNAc6S-GlcA-pNP | 15 | >98% | 1233.9 ± 0.7 | 1234.0 |
| 3 | GlcA-GalNAc-GlcA-GalNAc4S-GlcA-pNP | 9 | >98% | 1153.8 ± 0.7 | 1153.9 |
| 4 | GlcA-GalNTFA-GlcA-GalNAc-GlcA-pNP[2] | 30 | 59% | 1127.9 ± 0.7 | 1127.8 |
| 5 | GlcA-GalNTFA6S-GlcA-GalNAc6S-GlcA-pNP | 4 | 94% | 1287.5 ± 0.5 | 1288.0 |
| 6 | GlcA-GalNH$_2$-GlcA-GalNAc-GlcA-pNP | 20 | 90% | 1031.5 ± 0.6 | 1031.8 |

TABLE 1-continued

Summary of synthetized CS oligosaccharides up to 9-mer

| Compound | Abbreviated saccharide sequence | Amount (mg) | Purity[1] (%) | Measured Molecular Mass (Da) | Calculated molecular Mass (Da) |
|---|---|---|---|---|---|
| 7 | GlcA-GalNH$_2$6S-GlcA-GalNAc6S-GlcA-pNP | 4 | 96% | 1191.8 ± 0.6 | 1191.2 |
| 8 | GlcA-GalN$_{Az}$-GlcA-GalNAc-GlcA-pNP | 5 | >98% | 1057.6 ± 0.7 | 1057.8 |
| 9 | GlcA-GalNH$_{Az}$6S-GlcA-GalNAc6S-GlcA-pNP | 5 | >98% | 1217.6 ± 0.6 | 1217.9 |
| 10 | GlcA-GalNAc6S-GlcA-GalNAc6S-GlcA-GalNAc6S-GlcA-pNP | 30 | >98% | 1693.8 ± 1.1 | 1693.4 |
| 11 | GlcA-GalNAc-GlcA-GalNAc4S-GlcA-GalNAc4S-GlcA-pNP | 11 | 94% | 1613.3 ± 0.6 | 1613.3 |
| 12 | GlcA-GalNAc-GlcA-GalNAc-GlcA-GalNAc6S-GlcA-pNP | 5 | >98% | 1533.2 ± 0.5 | 1533.2 |
| 13 | GlcA-GalNAc-GlcA-GalNAc6S-GlcA-GalNAc6S-GlcA-pNP | 19 | >98% | 1613.3 ± 0.6 | 1613.3 |
| 14 | GlcA-GalNAc6S-GlcA-GalNAc6S-GlcA-GalNAc6S-GlcA-GalNAc6S-GlcA-pNP | 22 | >98% | 2153.5 ± 1.1 | 2152.7 |
| 15 | GlcA-GalNAc-GlcA-GalNAc4S-GlcA-GalNAc4S-GlcA-GalNAc4S-GlcA-pNP | 14 | >98% | 2073.6 ± 1.2 | 2072.7 |

[1]Purity was determined by high resolution anion exchange HPLC analysis.
[2]The product is a mixture of compound 4 and its detrifluoroacetylated product as demonstrated by ESI-MS analysis.

Figure 3A:
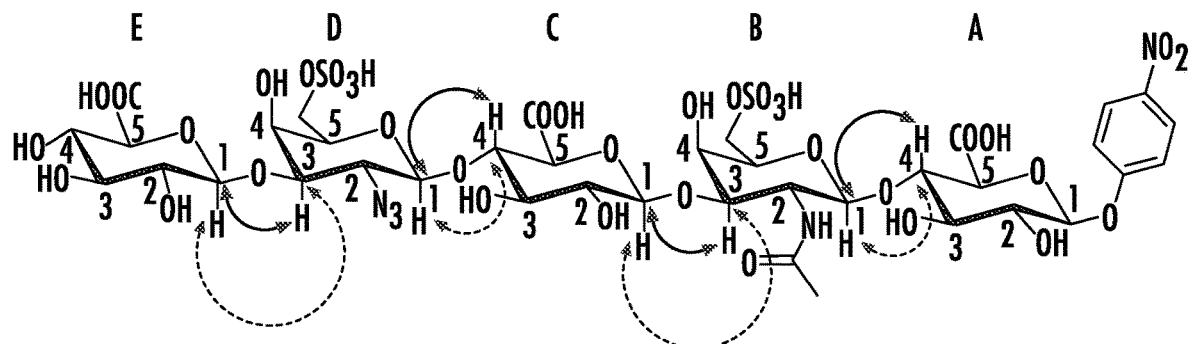
FIGS. 3A and 3B depict the results of structural analysis of one exemplary CS compound (compound 9), with FIG. 3A being a schematic illustration of compound 9 with chemical shifts, and FIG. 3B being a plot of heteronucluear multiple-bond correlation spectroscopy (HMBC) of 2D-NMR.
Figure 3B:
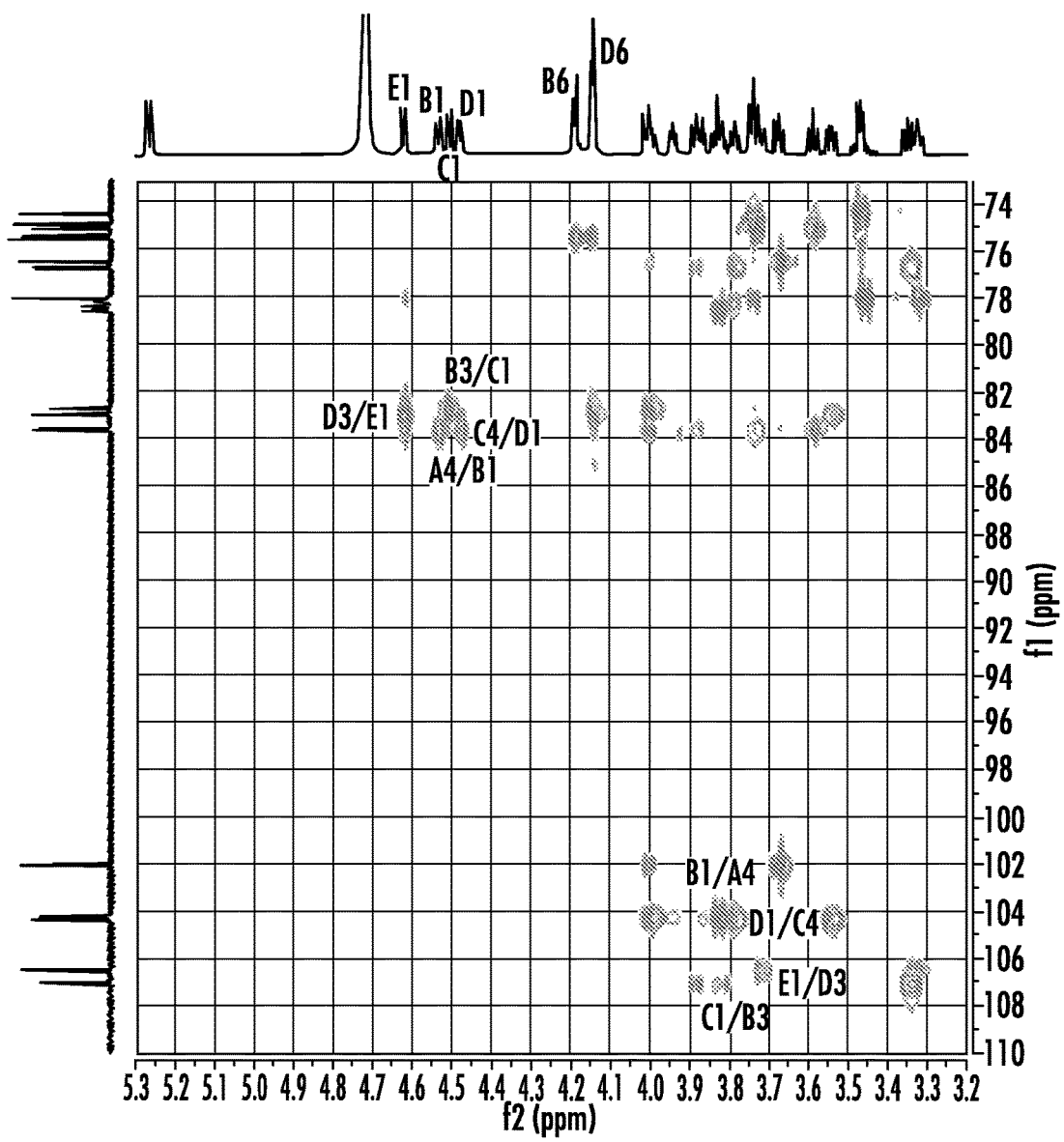

The purity and structure of products were characterized by high resolution anion-exchange HPLC, electrospray ionization mass spectrometry (ESI-MS) and NMR. The majority of products displayed a single symmetric peak on HPLC, confirming the purities (Table 1). The structure of each compound was confirmed by 1D- and 2D-NMR with full assignments. One representative example for the structural analysis of compound 9 using heteronucluear multiple-bond correlation spectroscopy (HMBC) of 2D-NMR is shown in FIG. 3B. Cross signal of residue anomeric proton of residue C and carbon (C-4) of residue B was observed (dashed double arrows in FIG. 3A); likewise cross signal of the proton (H-4) of residue B and anomeric carbon of residue C was also observed (solid double arrows in FIG. 3A). The cross peak signals suggest that the glycosidic linkage is 1→3 link. Using a similar approach, it was revealed that the glycosidic linkage between residue E and D is also 1→3 link. The anomeric proton-proton coupling constant ($^3J_{H-H}$) values of residue B, C, D and E were determined to be 8.5, 7.9, 8.2 and 7.9 Hz, respectively, from 1 D-NMR analysis. The measured $^3J_{H-H}$ values suggest that the glycosidic linkages in compound 9 are in the β-form. Comparing the chemical shifts of H-6 from residues D and B in compound 9 and compound 8 revealed the presence of 6-O-sulfation in compound 9. The chemical shifts of H-6 were changed to 4.19 ppm (residue B, compound 9) from 3.72-3.74 ppm (residue B, compound 8), and 4.14-4.15 ppm (residue D, compound 9) from 3.68-3.72 ppm (residue D, compound 8).

Thus, in some embodiments provided herein are novel methods to synthesize structurally homogeneous 4-O-sulfated and 6-O-sulfated CS oligosaccharides. The enzymatic approach is highly divergent to prepare a range of oligosaccharides merely using a small number of enzymes and cofactors. These methods, as shown herein, can be suitable for the preparation of structurally diversified CS oligosaccharide libraries. Prior to the instant disclosure the enzymatic synthesis of CS was perceived as unable to prepare a sufficiently large quantity of structurally defined CS oligosaccharides for biological evaluations and studies. By way of example and not limitation, the disclosed enzymatic methods of synthesizing CS can yield milligram to gram quanitites, ranging from about 4 milligrams to about 40 milligrams, or more. In some aspects, the disclosed synthetic routes can yield at least about 30 milligrams or more. In some aspects, the disclosed synthetic routes can yield industrially applicable quantities, including for example at least about 1 gram or more, or about 1 gram to about 100 grams or more.

In development of the disclosed methods of CS synthesis significant challenges were overcome, including for example improving the accessibility of recombinant CS biosynthetic enzymes and reducing the production cost for UDP-GalNAc. In addition to synthesizing natural CS oligosaccharides, the instant disclosure provides for the possibility of preparing unnatural 6-O-sulfated CS oligosaccharides. The synthesis was accomplished in multi-milligram scales, allowing complete structural characterization by MS and NMR. In addition to CS-A and CS-C, CS-D and CS-E were also synthesized by methods disclosed herein. The demonstration of the enzymatic synthesis of structurally defined CS oligosaccharides offers an essential tool to investigate the biological functions of CS.

In addition to the CS compounds ranging from trisaccharides to nonasaccharides, i.e. 9-mers, as shown in Table 1 and FIG. 1, the disclosed methods provide for the synthesis of larger and/or longer CS compounds, as shown in FIGS. 4, 5A, 5B, 6A, 6B, 7A, 7B, and 8, and below.

Figure 4:
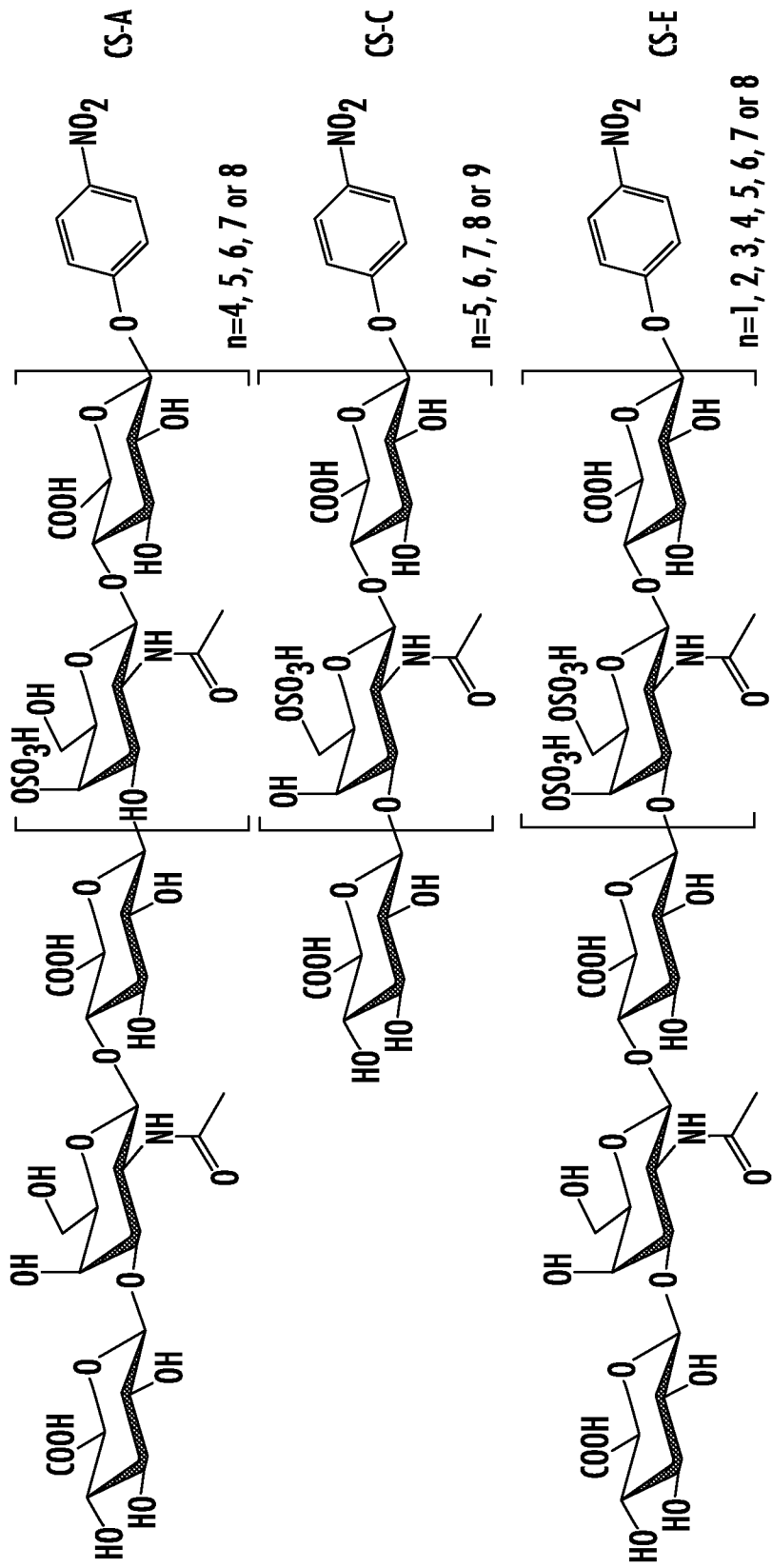
FIG. 4 is a schematic illustration of exemplary CS compounds, namely CS-A, CS-C and CS-E, synthesized according to the presently disclosed methods, and shown in an abbreviated chemical structure format.
Figure 5A:
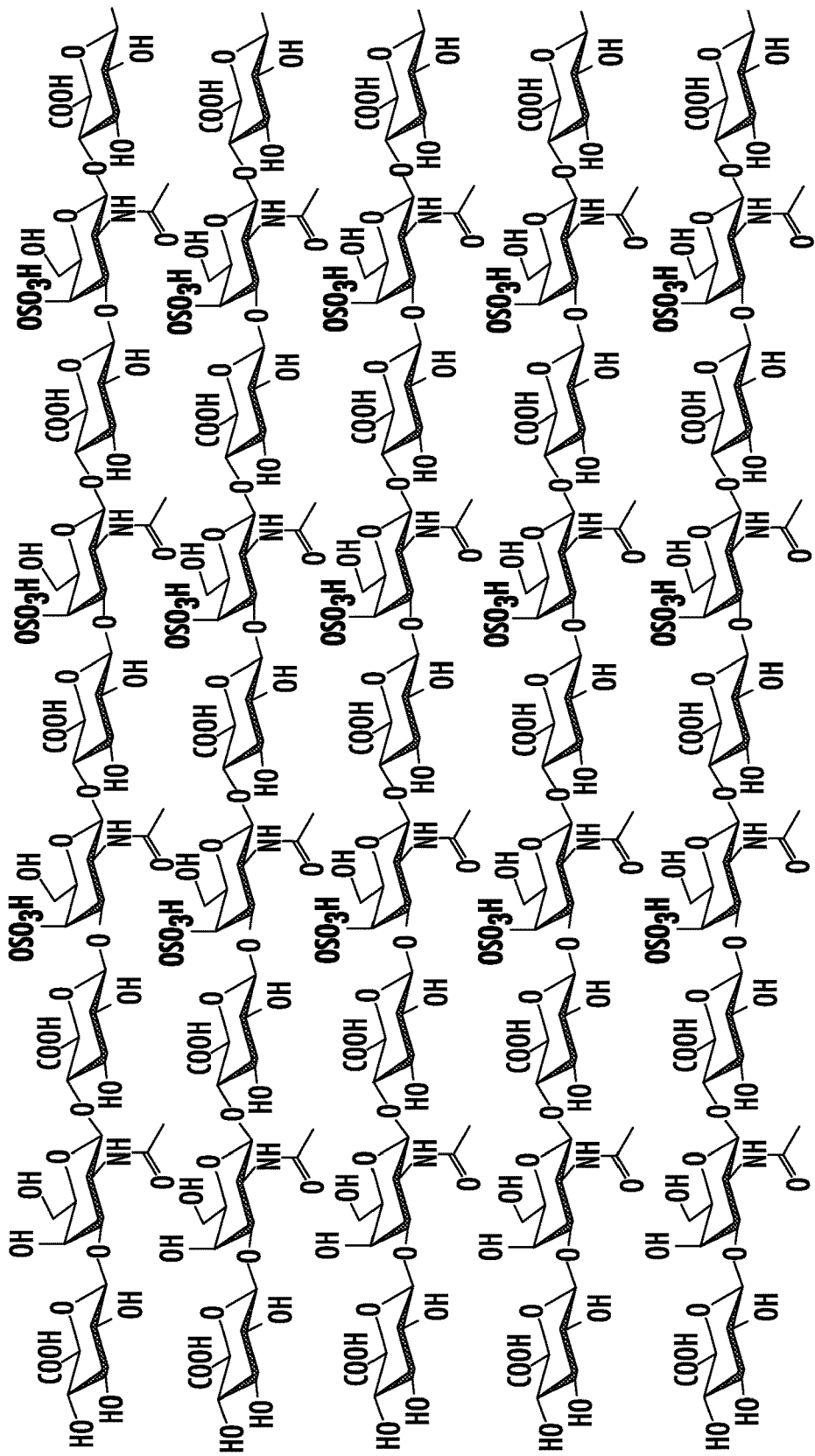
FIGS. 5A and 5B are schematic illustrations of the full chemical structures of exemplary CS-A compounds.
Figure 5B:
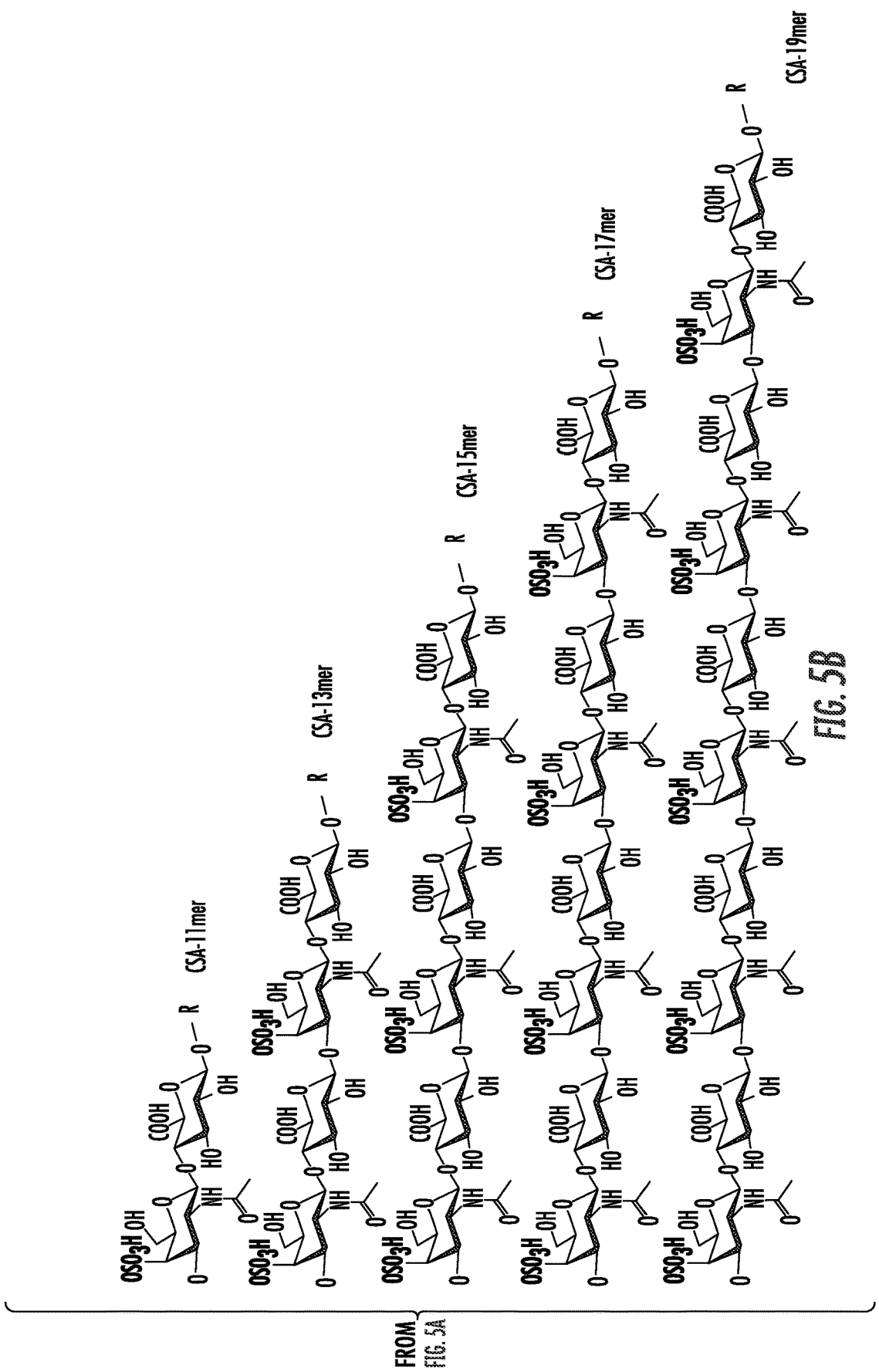
Figure 6B:
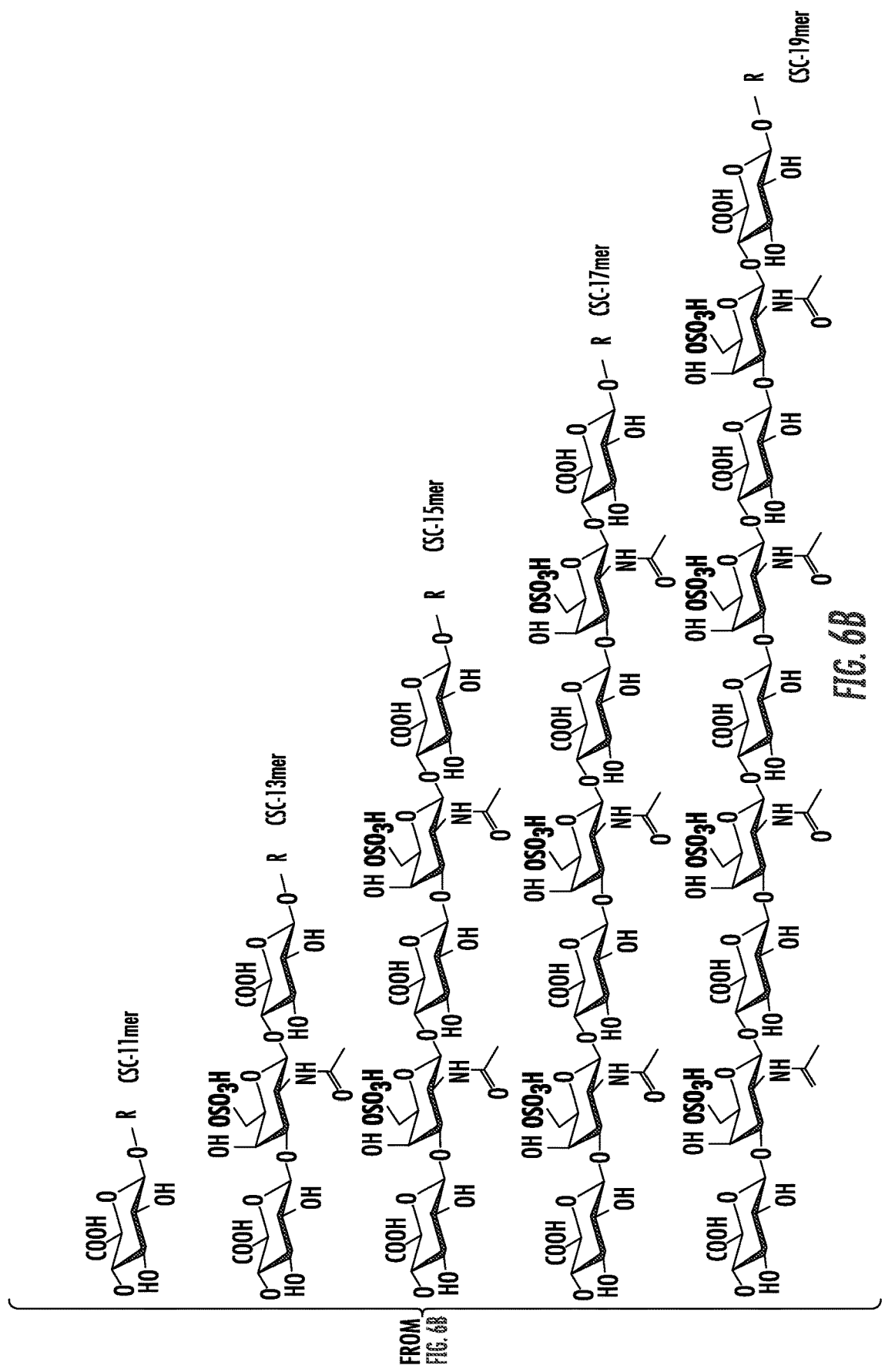
Figure 7A:
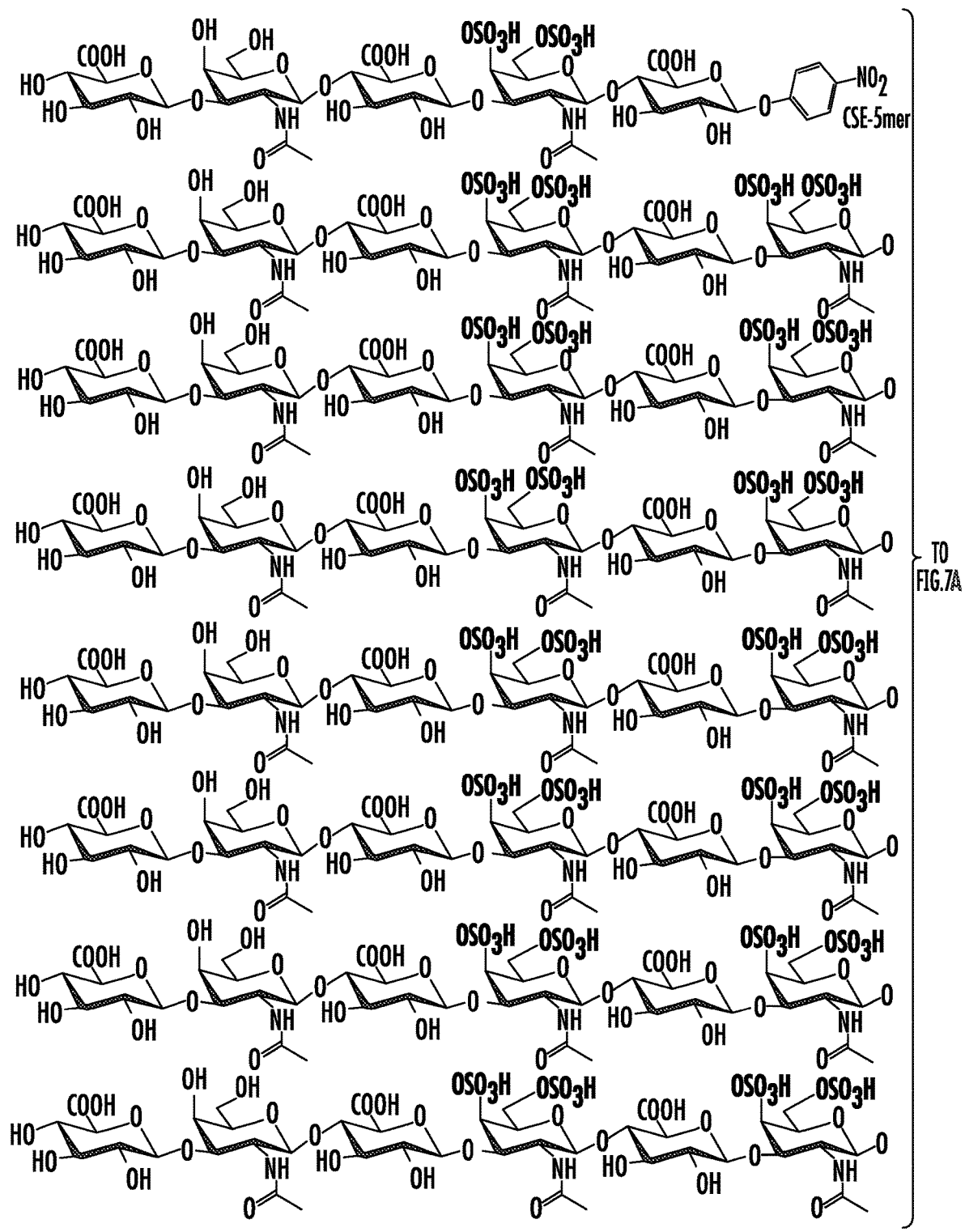
FIGS. 7A and 7B are schematic illustrations of the full chemical structures of exemplary CS-E compounds.
Figure 7B:
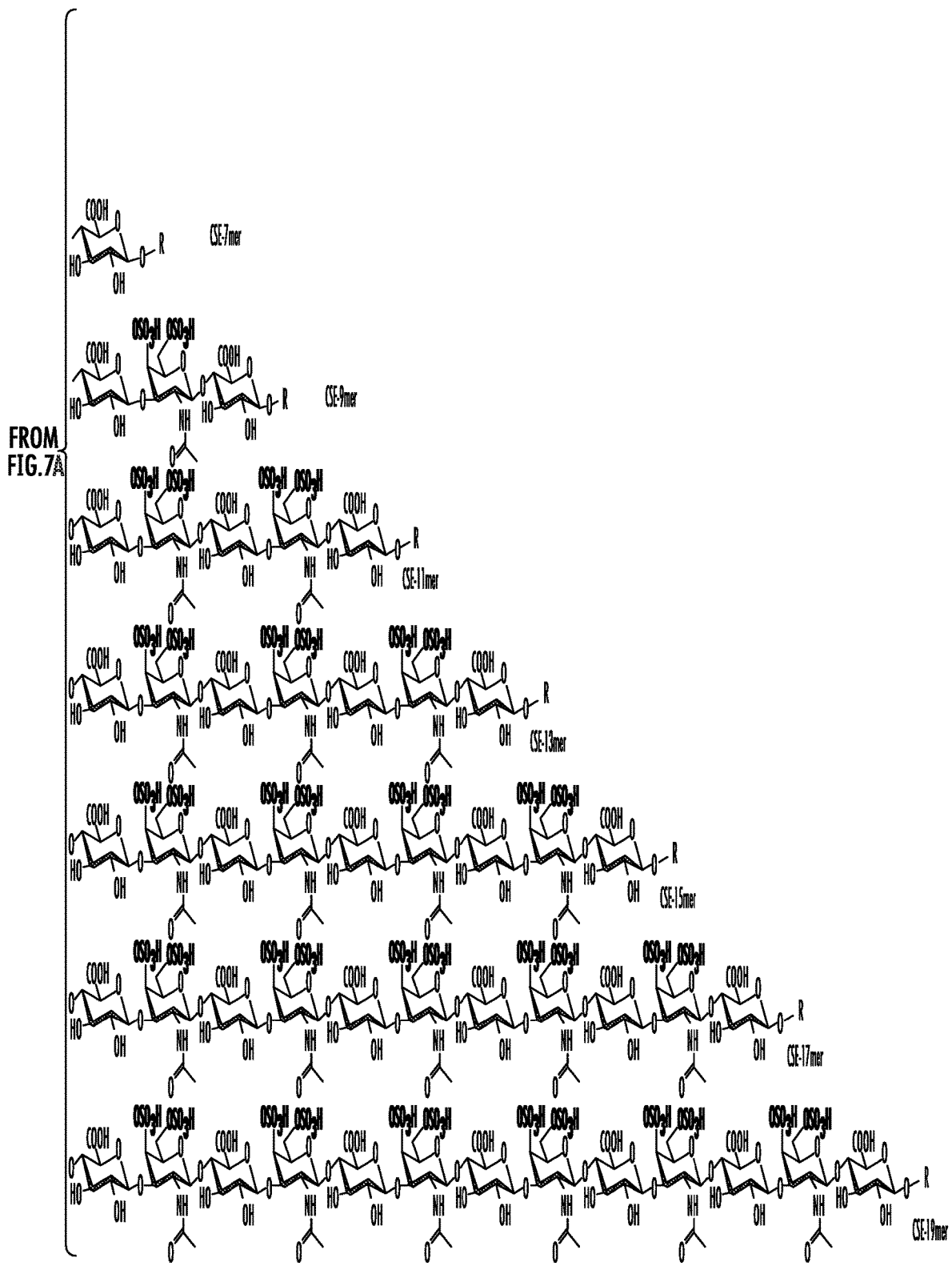

Example CS-A Oligosaccharides (11-Mer to 19-Mer):

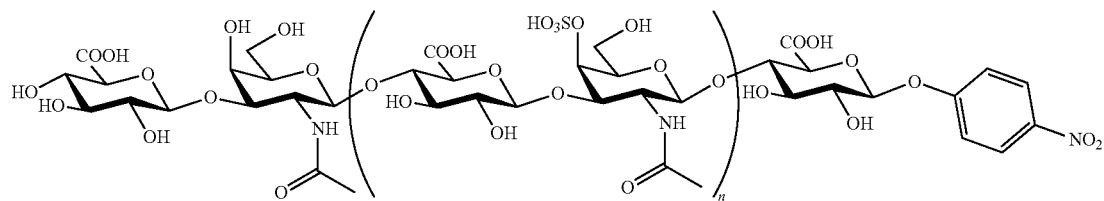

n=4, CS-A 11-mer
n=5, CS-A 13-mer
n=6, CS-A 15-mer
n=7, CS-A 17-mer
n=8, CS-A 19-mer Example CS-C Oligosaccharides (11-Mer to 19-Mer):

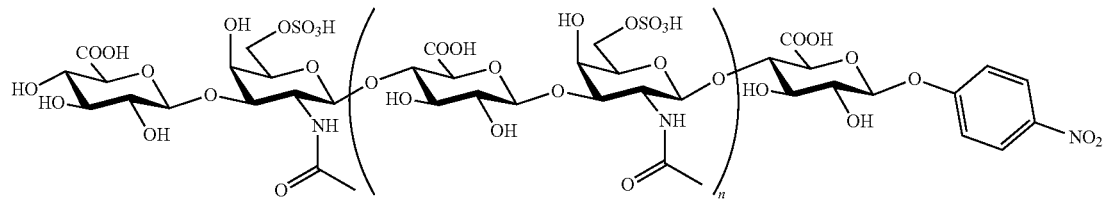

n=4, CS-C 11-mer
n=5, CS-C 13-mer
n=6, CS-C 15-mer
n=7, CS-C 17-mer
n=8, CS-C 19-mer Example CS-E Oligosaccharides (5-Mer to 19-Mer):

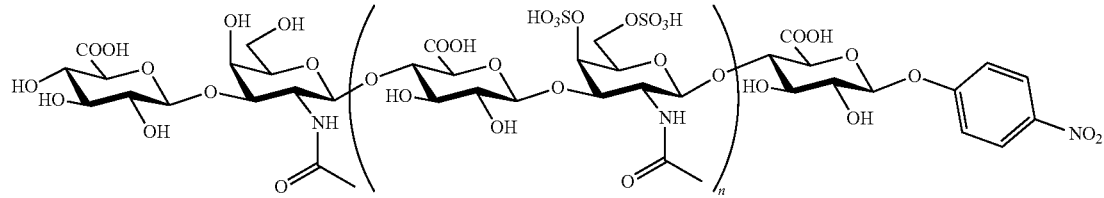

n=1, CS-E 5-mer
n=2, CS-E 7-mer
n=3, CS-E 9-mer
n=4, CS-E 11-mer
n=5, CS-E 13-mer
n=6, CS-E 15-mer
n=7, CS-E 17-mer
n=8, CS-E 19-mer FIG. 4 also shows a plurality of CS-A, CS-C and CS-E compounds synthesized by the disclosed methods and schematics. These CS compounds are shown in an abbreviated form in FIG. 4, with the full CS structures shown in FIGS. 5A, 5B, 6A, 6B, 7A and 7B.

Figure 8:
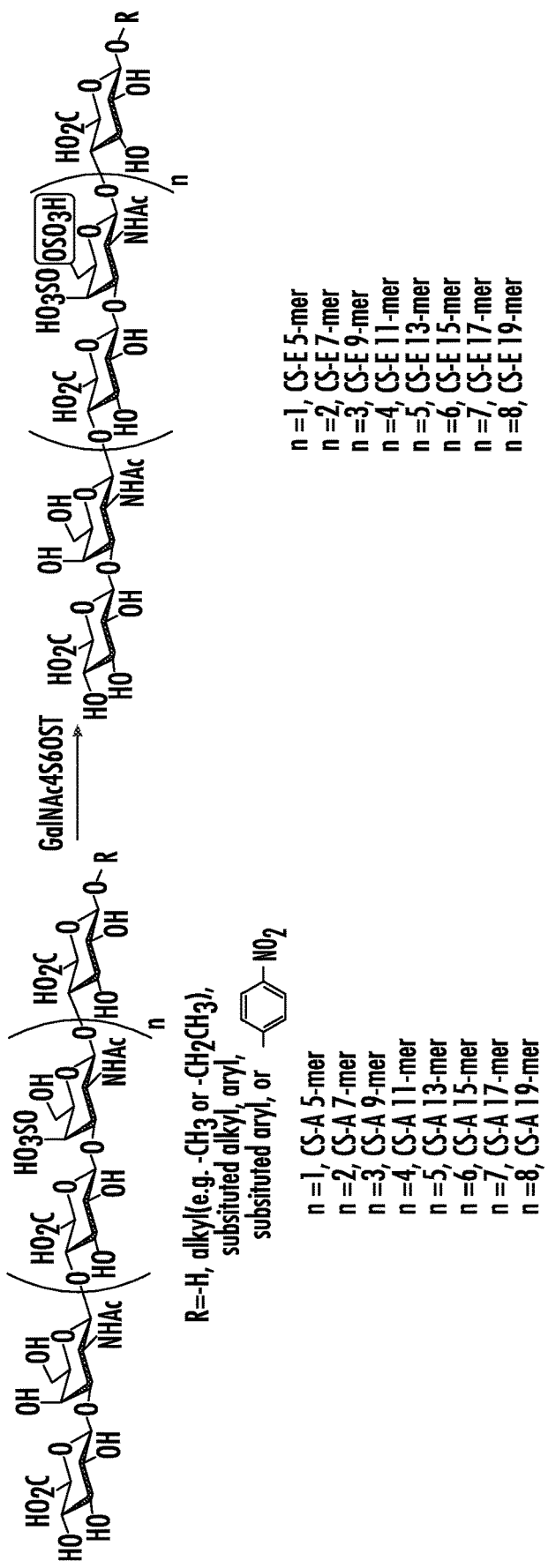
FIG. 8 is a schematic illustration of a synthetic route to synthesize CS-E from CS-A.

Approaches for synthesizing CS-D and CS-E were developed as disclosed herein. Such methods utilize similar approaches as with the synthesis of CS-A and CS-C, but with additional enzymatic steps. For example, in some embodiments the synthesis of CS-D and/or CS-E requires additional CS sulfotransferases, including for example CS 2-O-sulfotransferase (to prepare CS-D) and GalNAc4S-6-O-sulfotransferase (to prepare CS-E). The instant disclosure provides both 2-O-sulfotransferase and GalNAc4S-6-O-sulfotransferase needed for such additional steps. By way of example and not limitation, FIG. 8 illustrates a method of synthesizing CS-E from CS-A to yield CS-E compounds ranging from 5-mer to 19-mer. In such methods, for example, GalNAc4S6OST can convert a CS-A compound to a CS-E compound.

Thus, in some embodiments, disclosed herein are methods of synthesizing chondroitin sulfate oligosaccharides. Such methods can comprise in some embodiments providing a chondroitin backbone and completing at least two, or three, or four of the following enzymatic reaction steps in FIG. 1, including for example an elongation step to add a GalNAc residue using a glycosyltransferase from *E. coli* K4 (KfoC), an elongation step to add a GlcA residue using KfoC, a 6-O-sulfation step using chondroitin sulfate 6-O-sulfotransferase (CS6OST) and sulfate donor 3'-phosphoadenosine 5'-phosphosulfate (PAPS), and/or a 4-O-sulfation step involving chondroitin sulfate 4-O-sulfotransferase (CS4OST) and PAPS. Such methods can in some aspects further comprise a step of transferring a GalNTFA residue to a trisaccharide backbone by a KfoC to yield a tetrasaccharide. In some aspects each of these reaction steps can be performed more than once, as illustrated in FIGS. 1, 2A and 2B.

Such methods can yield substantially homogenous chondroitin sulfate oligosaccharides, including for example 4-O-sulfated and/or 6-O-sulfated chondroitin oligosaccharides having a size ranging from a trisaccharide to a nonasaccharide. In some aspects the synthesized chondroitin sulfates can have a size ranging from a 3-mer to a 15-mer, or more. Such methods can also yield unnatural chondroitin sulfate oligosaccharides. Such methods can also yield structurally defined chondroitin sulfate oligosaccharide, in some aspects in multi-milligram quantities. In some aspects, such synthetic chondroitin sulfate oligosaccharides can include chondroitin sulfate A (CS-A), chondroitin sulfate C (CS-C), chondroitin sulfate D (CS-D) and chondroitin sulfate E (CS-E), including those depicted in FIGS. 1, 4, 5A, 5B, 6A, 6B, 7A, 7B, and 8.

In FIGS. 1, 2A, 2B, 5A, 5B, 6A, 6B, 7A, 7B, and 8, the R group can in some embodiments be selected from the group consisting of —H, alkyl (such as but not limited to —CH$_3$ or —CH$_2$CH$_3$), substituted alkyl, aryl, and substituted aryl (such as but not limited to a p-nitrophenyl group). In some embodiments, the R group can include a pNP compound as shown, for example, in FIGS. 3 and 4, and hereinabove. However, the illustration of the compounds hereinabove and in FIGS. 3 and 4 with the pNP constituent is for illustrative purposes only, as such compounds can alternatively include an R group as defined hereinabove.

Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

As used herein the term "alkyl" refers to C$_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

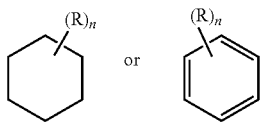

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

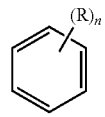

wherein n is an integer from 0 to 2 comprises compound groups including, but not limited to:

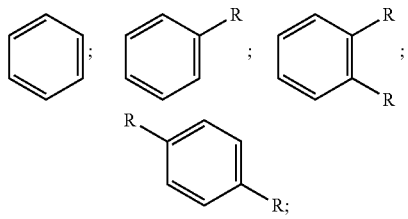

and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "heterocycle" refers to a non-aromatic or aromatic, monocyclic or multicyclic ring system of about 3 to about 14 atoms, wherein at least one of the atoms is a heteroatom (e.g., oxygen, nitrogen, or sulfur). The term "N-heterocycle" refers to a heterocycle wherein at least one of the heteroatoms is a nitrogen atom. Examples of N-heterocycles include, but are not limited to, azetidine, pyrrolidine, pyrrole, pyrroline, piperidine, pyridine, piperazine, pyrazine, pyrimidine, pyridazine, morpholine, and thiazine.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

As used herein, the term "acyl" refers to an organic carboxylic acid group wherein the —OH of the carboxyl group has been replaced with another substituent (i.e., as represented by RC(=O)—, wherein R is an alkyl, substituted alkyl, aralkyl, aryl or substituted aryl group as defined herein). As such, the term "acyl" specifically includes arylacyl groups, such as an acetylfuran and a phenacyl group. Specific examples of acyl groups include acetyl and benzoyl.

"N-acyl" refers to a group having the structure —N—C (=O)—R, wherein R is as defined for acyl. These groups can also be referred to as amides. Modified N-acyl groups include compounds wherein the oxygen of the N-acyl has been replaced by S or NH, as well as to compounds wherein the carbonyl group (i.e., the —C(=O)—) is attached to a second heteroatom in addition to the nitrogen. For example, the carbonyl can be attached to a second nitrogen atom to form a urea linkage (i.e., —NH—C(=O)—NH—R).

The term "amino" refers to the —NH$_2$, the —NHR, and the —NR$_2$ groups, wherein each R is independently alkyl, substituted alkyl, aryl, substituted aryl, or aralkyl, as well as to amino and ammonium functionalities in N-heterocycles (e.g., morpholine, etc). As used herein the term "amino" can also refer to substituents that provide quaternary ammonium cations, such as —$^+$NH$_3$, —$^+$NH(R)$_2$, and —$^+$N(R)$_3$ groups, wherein each R is independently alkyl, substituted alkyl, aryl, substituted aryl or aralkyl.

The term "ester" refers to a moiety comprising an —O—C(=O)—R group, wherein R can be alkyl, substituted alkyl, aralkyl, aryl, or substituted aryl. In some embodiments, the R group can include an amino substituent and the ester is an amino ester.

The term "amide" refers to a moiety comprising a —N(R')—C(=O)—R group, wherein R is selected from alkyl, substituted alkyl, aralkyl, aryl or substituted aryl and R' is H, alkyl, substituted alkyl, aralkyl, aryl, or substituted aryl.

The term "urea" as used herein can refer to a moiety comprising a —N(R')—C(=O)—N(R')— group, wherein each R' is independently H, alkyl, substituted alkyl, aralkyl, aryl, or substituted aryl.

The term "hydroxyl" refers to the —OH group.

When the term "independently selected" is used, the substituents being referred to (e.g., R groups, such as groups R$_1$ and R$_2$, or groups X and Y), can be identical or different. For example, both R$_1$ and R$_2$ can be substituted alkyls, or R$_1$ can be hydrogen and R$_2$ can be a substituted alkyl, and the like.

EXAMPLES

The following Examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Experimental Procedures

Construction of Expression Plasmids for KfoC, AGX1, CS6OST and CS4OST

Both KfoC (coding the chondroitin polymerase) and agxI (coding the UDP-N-acteylglucosamine pyrophosphorylase 1) were cloned into pET15b vector (Novagen) to construct Nterminal (His)$_6$-tagged proteins. The 2.1 kb DNA containing the whole kfoC gene was amplified from E. coli K4 genome using primer pair KfoC-F and KfoC-R. Phusion high fidelity DNA polymerase (NEB) was used to keep the fidelity. The PCR product was cloned into the NdeI/BamHI sites using HiFi DNA assembly master mix (NEB) to give the expression plasmid pET15b-kfoC. Sequencing was applied to ensure the correctness of the gene (Eurofins Genomics). Using the similar strategy, the 1.5 kb agxI gene was amplified from human cDNA clone UAP1 (Origene) using primer pair AGX1-F and Agx1-R. The DNA fragment was cloned into pET15b NdeI/BamHI sites using the same method as cloning kfoC. The constructed agxI expression plasmid pET15b-agx1 was also subjected to sequencing to make sure the gene is correct.

To express the chondroitin sulfotransferase, the genes responsible for human CS4OST and mouse CS6OST were cloned into pFastBac-Mel-HT vector. For CS4OST, primer pair hCS-4-OST-1-F and hCS-4-OST-1-R were used to PCR amplify the CS4OST coding gene from cDNA clone IMAGE 1283775. The 1.0 kb PCR product was cloned into pFastBac-Mel-HT EcoRI/XbaI sites using HiFi DNA assembly master mix (NEB) to generate the recombinant plasmid pFastBa-Mel-HT-CS4OST. For CS6OST, PCR was also applied with mCS-6-OST-F and mCS-6-OSTR as the primer pair, cDNA clone IMAGE 6493234 as the template. The resultant 1.3 kb PCR product was inserted into the EcoRI/XbaI sites of pFastBac-Mel-HT using the same strategy for cloning CS4OST coding gene to afford plasmid pFastBac-Mel-HT-CS6OST.

Expression of Recombinant KfoC, AGX1, CS4OST and CS6OST

The expression of KfoC and AgxI were performed in E. coli BL21 cells. The expression plasmids pET15bkfoC and pET15b-agx1 were transformed into E. coli BL21 competent cells (Invitrogen). The transformed cells were grown in LB medium containing 50 µg/L kanamycin and incubated at 37° C. until the OD600 reached 0.6-0.8. Then a final concentration of 0.2 mM isopropylthiogalactopyranoside (IPTG) was added to induce the expression of the proteins. The cultures were kept at 22° C. and 195 rpm overnight. The E. coli cells were harvested by centrifuge with 6,000 rpm for 10 min, then resuspended in 25 mM Tris, 30 mM imidazole, and 500 mM NaCl, pH 7.5. Sonication was used to lysis the cell, and subsequent centrifuge was at 14,000 rpm for 30 min. The supernatant was subjected to a nickel agarose column (GE Healthcare). Buffer A (25 mM Tris, 60 mM imidazole, and 500 mM NaCl, pH 7.5) was used to wash the column and buffer B (25 mM Tris, 250 mM imidazole, 500 mM NaCl, pH 7.5) was used to elute the proteins. All the proteins were kept in 20% glycerol at −80° C.

The expression of CS6OST and CS4OST was carried out in the Sf9 cells (Invitrogen) using Sf-900™ III SFM media (Life Technologies). The sequencing correct plasmids (pFastBac-Mel-HT-CS6OST and pFastBac-Mel-HT-CS4OST) were transformed into E. coli DH10Bac cells (Invitrogen). The recombinant viruses for expression of CS6OST and CS4OST were made following the instruction manual (Invitrogen). Infection of the recombinant virus for expression of CS6OST and CS4OST was carried out when the insect cells were at a concentration of 2.0×10$_6$ cells/mL. The culture was incubated in the shaker at 27° C. for another 4 to 5 days. Culture was harvested by centrifuge (4,000 rpm, 10 min) and the supernatant was added 1 mM phenylmethanesulfonyl fluoride (PMSF), 0.1% Triton X-100 and 2% glycerol, adjusted the pH to 7.0 by NaOH solution. Another centrifuge (8,000 rpm, 30 min) was applied to remove the precipitates. The supernatant culture was then mixed with an equal volume of 20 mM 3-(N-morpholino) propanesulfonic acid (MOPS) buffer containing 0.1% triton X-100, 2% Glycerol pH 7.0) filtered, and loaded to a heparin toyopearl (Tosoh Bioscience) column. Buffer C (20 mM MOPS, 100 mM NaCl, 2% glycerol and 0.1% reduced triton X-100 (Sigma), pH 7.0) was used to wash the column until UV absorbance at 280 nm reached baseline. Gradient elution of 0-100% Buffer D (20 mM MOPS, 1 M NaCl, 2% glycerol and 0.1% reduced triton X-100, pH 7.0) was used to elute the target proteins. The collections with chondroitin sulfotransferase activity were collected. To further purify the chondroitin sulfotransferases and remove the chondroitinase produced by the insect cells, the collected proteins were then dialyzed by the nickel column buffer A and then load to a cobalt (for CS4OST) or a nickel column (for CS6OST). A gradient elution of 0-100% nickel column buffer B was applied to elute the proteins. The collected proteins with chondroitin sulfotransferase activity were kept in 20% glycerol at −80° C.

Measurement of the Activities of CS4OST and CS6OST

Chondroitin sulfotransferase activity of the proteins was determined by incubating 2-5 μl purified proteins with 5 μg chondroitin (Seikagaku) and 1-5×10$_5$ cpm of [35S]PAPS (5 μM) in 100 μl buffer containing 50 mM MOPS (pH 7.0). The reaction was incubated at 37° C. for 2 hours and quenched by adding 400 μl UPAS buffer (50 mM NaAcO, 150 mM NaCl, 4 M Urea, 1 mM EDTA and 0.1% Triton X-100, pH5.5). Then the samples were loaded to 200 μl DEAE-sepharose columns and washed by 4 ml UPAS buffer, 4 ml washing buffer (50 mM NaAcO, 250 mM NaCl and 0.1% Triton X-100, pH5.5). The [35S]-chondroitin was eluted by the elution buffer (50 mM NaAcO, 1 M NaCl and 0.1% Triton X-100, pH5.5) and subjected to liquid scintillation counting.

Measurement of the Activity of Chondroitinase

It might be desirable to measure the level of contaminated viral chondroitinase in the recombinant CS4OST and CS6OST preparations. Briefly, 0.1 mg chondroitin was incubated with 5 μl culture or purified enzyme in a total of 50 μl a buffer containing 50 mM MOPS (pH7.0) at 37° C. overnight. Then the reaction mixture was diluted 10 times and tested the absorbance at the UV 232 nm.

Preparation UDP-GalNAc and UDP-GalNATFA

To synthesis UDP-N-acetylgalactosamine (UDP-GalNAc), one of the chondroitin biosynthesis cofactors, the substrate N-acetyl-D-galactosamine (GalNAc, Carbosynth) 4 mmol was incubated with 5 mMol ATP, 4.5 mmol UTP, 45 mg NAHK, 36 mg AGXI and 4.2 mg pyrophosphatase in a buffer containing 50 mM Tris-HCl buffer (pH 7.5), 10 mM MgSO$_4$ in a total volume of 200 mL. The reaction mixture was incubated at 37° C. overnight and the product UDP$_{Page}$ GalNAc was monitored by HPLC and ESI-MS. The synthesis of UDP-GalNTFA, 3.6 mmol GalNTFA, was incubated in the same reaction system and conditions used for synthesis of UDP-GalNAc. GalNTFA is prepared according to the literature.

Conversion of GalNTFA to GalNH$_2$ and GalN$_{AZ}$

To obtain compound 4 with a GalNTFA unit in the chondroitin backbone, the synthesis was initiated from chondroitin trisaccharide. The conversion of chondroitin trisaccharide to compound 4 involved 2 steps elongation. In summary, 100 mg trisaccharide backbone was incubated with 0.3 mmol UDP-GalNTFA, 25 mg KfoC in the same buffer as that used for elongation of the chondroitin backbone. The resultant tetrasaccharide with a GalNTFA unit at the nonreducing end was purified by a C18 column (Biotage) and then used as the substrate for compound 4. At this step, the GlcA residue was added at the presence of KfoC, in the elongation buffer as mentioned before. Compound 4 was also purified by a C18 column at the same condition used for purification of chondroitin backbone. To get rid of the salt in the solution, compound 4 was further purified by a P2 column.

To convert the GalNTFA residue to GalNH$_2$ residue, LiOH solution was added to compound 4 solution (about 1 mg/ml) in a total volume of 50 ml to reach the final concentration of 0.1 M. HPLC with a Polyamine II column and MS were used to monitor the degree of the detrifluoroacetylation reaction. Upon the completion of detrifluoroacetylation, the pH of the reaction mixture was adjusted to 2.0 for purification by a C18 column. Then compound 6 was further purified by a P2 column.

Synthesis of compound 8 was completed from compound 6. To a solution of compound 6 in water (2 mL, 10 mg/mL), MeOH (20 mL) was added, along with 0.5 mL of a Cu(II) SO4.5H2O solution in water (1 mg/mL) and Et$_3$N (50 μL). After mixing, Imidazole-1-sulfonyl azide hydrochloride (prepared according to the literature 3) was added (41 mg, 10 equiv) and the reaction was left agitated for 48 h. The produced compound 8 was subjected to a Giga Q chromatography (Tosoh Bioscience) and then a BioGel P2 column (BioRad) for purification.

Example 1

Synthesis of Chondroitin Backbone

Compound 1 was synthesized from chondroitin trisaccharide backbone. Briefly, 10 mg trisaccharide was incubated with 0.1 mmol 3'-phosphoadenosine 5'-phosphosulfate (PAPS) in 100 ml buffer containing 50 mM MOPS (pH 7.0) and 10 ml purified CS6OST, 37° C. overnight. HPLC equipped with Polyamine II column (YMC) was used to monitor the reaction. Then, the product compound 1 was subjected to a column with Toyopearl GigaCap Q-650 resin (Tosoh Bioscience) for purification. The elution of the Giga Q column was using a gradient of 0-100% buffer B (1M NaCl, 20 mM Tris-HCl, pH 7.0) from Buffer A (20 mM Tris-HCl, pH 7.0) in 120 minutes, at the flow rate of 0.7 ml/min. The collected compound 1 was then dried, dissolved in 2 ml H$_2$O and subjected to a semi-preparative polyamine II column (250×4.6 mm, S-5 μm, YMC). The elution condition was used as follows: the gradient elution was 40-100% KH$_2$PO$_4$ (1M) buffer in 40 min at flow rate 1 ml/min. The collection was further purified by a Bio-Gel P2 column using 0.1 M ammonium bicarbonate (Sigma) at a flow rate of 4 mL/h. The resultant compound 1 was then analyzed by MS and NMR spectra.

Example 2

Synthesis of CS Compounds

The synthesis of compound 2 was started from chondroitin pentasaccharide. Briefly, 39 mg pentasaccharide backbone was incubated with 0.24 mmol PAPS, 10 mL purified CS6OST in a total 100 mL volume containing 50 mM MOPS (pH 6.8), 37° C. overnight. The completion of the reaction was monitored by injecting a small amount of reaction mixture to HPLC using Polyamine II column. If reaction was not complete, additional CS6OST enzyme and PAPS was added, and kept the reaction at 37° C. for another day. The product compound 2 was purified by Giga™ Q column and P2 column subsequently using the same conditions as those for purification of compound 1. Then compound 2 was subjected to MS and NMR analysis.

Compound 3 was synthesized from pentasaccharide backbone. Briefly, 20 mg chondroitin pentasaccharide was incubated with 0.07 mmol PAPS, 7 ml CS4OST in a total 200 ml buffer containing 50 mM MES (pH 6.5), 2 mM dithiothreitol (DTT) and 20 mM CaCl$_2$) at 37° C. overnight. The synthesized compound 3 was purified sequentially by a Giga™ Q column, a semi-preparative polyamine II column and a BioGel P2 column.

Compound 5 has C-6 sulfation of the GalNAc residues of compound 4. Here, 6 mg compound 4 was incubated with 0.03 mmol PAPS and 5 ml CS6OST in 50 ml reaction buffer containing 50 mM MOPS (pH 6.8). After incubation at 37° C. overnight, the product was purified by a Giga™ Q column and subsequently a P2 column, following the conditions mentioned before.

To obtain compound 7, 10 mg compound 6 was incubated with 0.05 mmol PAPS in a reaction mixture containing 10 ml CS6OST, 50 mM MOPS (pH 6.8), at 37° C. for 2 days. The resultant compound 7 was purified by a Giga Q column, a semi-preparative polyamine II column and a subsequent P2 column, as conditions for purification of compound 1.

To obtain compound 9, compound 8 (about 7 mg) was further sulfated by 5 ml CS-6OST in the 50 ml reaction mixture containing 0.03 mmol PAPS and 50 mM MOPS (pH 6.8). The reaction mixture was incubated at 37° C. overnight, and the resultant compound 9 was purified by a Giga Q column and a subsequent P2 column.

To obtain compound 10, 29 mg chondroitin heptasaccharide was incubated with 0.24 mmol PAPS, 5 ml CS-6OST in 100 ml buffer containing 50 mM MOPS (pH 6.8) at 37° C. overnight. The HPLC results showed that the reaction was not complete, so another 4 ml CS-6OST was added into the reaction mixture. The reaction was incubated at 37° C. for another day until the reaction was almost complete. The purification of compound 10 was subjected to a Giga Q column with a gradient elution of 20-100% buffer B (1M NaCl, 20 mM sodium acetate, pH 5.0) from Buffer A (20 mM sodium acetate, pH 5.0) in 120 minutes, at the flow rate of 1 ml/min. The collected product was then dried and dialyzed to remove the salt for MS and NMR analysis.

To obtain compound 11, 18 mg chondroitin heptasaccharide backbone was incubated with 0.1 mmol PAPS, 7 ml CS4OST in 200 ml buffer containing 50 mM MES (pH 6.5), 2 mM DTT and 20 mM $CaCl_2$) at 37° C. overnight. The produced compound 11 was purified by a Giga Q column under the same condition for compound 10 and then dialyzed for MS and NMR analysis.

The synthesis of compound 12 from compound 1 involves 4 steps elongation, including alternative add GalNAc and GlcA units two times to the non-reducing end. The product after each step was analyzed by HPLC, MS and purified by a Giga Q column following the condition used for purification of compound 10. The final product compound 12 was further subjected to dialysis to remove the salt.

The conversion of compound 2 to 13 involved 2 steps elongation to add GalNAc and GlcA residues to the non-reducing end of compound 2 using the same conditions as those for synthesis of chondroitin backbone. After each step, the products was purified by Giga Q chromatography as compound 10 and desalted by dialysis if it was needed.

To generate compound 14, 22 mg nanosaccharide was incubated with 0.16 mmol PAPS, 15 ml CS-6OST in a total 100 ml volume containing 50 mM MOPS (pH 6.8), 37° C. overnight. The product compound 14 was purified by Giga Q column and then subjected to dialysis for desalination.

The synthesis of compound 15 was initiated from 20 mg chondroitin nonasaccharide backbone. It was incubated with 0.1 mmol PAPS, 7 ml CS4OST, 50 mM MES (pH 6.5), 2 mM DTT and 20 mM $CaCl_2$) in a total volume of 200 mL. The reaction mixture was kept at 37° C. overnight. The product was subjected to a Giga™ Q chromatography and subsequent dialysis.

Example 3

HPLC Analysis of CS Compounds

HPLC analysis of the chondroitin compounds was carried out via a Polyamine II column. Gradient elution was applied for elution. For the chondroitin backbones, the concentration of $KH_2PO_4$ buffer (1M) was increased from 0 to 50% in 20 min at flow rate 0.5 ml/min. The detect UV was set at 310 and 260 nm. For the chondroitin A and chondroitin C oligosaccharides, the concentration of $KH_2PO_4$ buffer (1M) was increased from 0 to 100% in 20 min at flow rate 1 ml/min. The oligosaccharides were detected at 310 nm absorption.

Example 4

ESI-MS Analysis of CS Compounds

The analyses were performed at a Thermo LCQ-Deca. CS oligosaccharides were directly diluted in 500 µl $H_2O$. A syringe pump (Harvard Apparatus) was used to introduce the sample by direct infusion (50 µl $min_{-1}$). Experiments were carried out in negative ionization mode. The electrospray source was set to 3 KV and 150° C. The automatic gain control was set to $1 \times 10_7$ for full scan MS. The MS data were acquired and processed using Xcalibur 1.3.

Example 5

NMR Analysis of CS Compounds

NMR experiments were performed at 298 K on Bruker Avance™ 700 MHz and 850 MHz spectrometer with Topsin™ 3.2 software. Samples (0.5 to 3.0 mg) were each dissolved in 0.5 ml $D_2O$ (99.996%, Sigma-Aldrich) and lyophilized three times to remove the exchangeable protons. The samples were re-dissolved in 0.5 ml $D_2O$ and transferred to NMR microtubes (O.D. 5 mm, Norrell). Chemical shifts are referenced to external 2,2-dimethyl-2-silapentane-5-sulfonate sodium salt (DSS, Sigma, Co.). 1D $_1$HNMR experiments "zg" pulse sequence were performed with 64 scans and an acquisition time of 3.8 sec. 1D $_{13}$C-NMR experiments "zgdc30" pulse sequence were performed with 10,000 scans and an acquisition time of 1.0 sec. 2D $_1$H-$_{13}$C HSQC experiments "hsqcgpph" pulse sequence were performed with 48 scans, 512 increments, 1.5 sec relaxation delay, and 120 msec acquisition time. 2D spectra were recorded with GARP carbon decoupling. 48 dummy scans were used prior to the start of acquisition. 2048 total points were collected in f2. $_{13}$C transmitter offset was set at 90.0 ppm.

REFERENCES

1. Mizumoto, S.; Yamada, S.; Sugahara, K., *Curr. Opin. Struct. Biol.* 2015, 34, 35-42.
2. Fried, M. W; Duffy, P. E., *Vaccine* 2015, 33, 7483-7488.
3. Chan, S.; Frasch, A.; Mandava, C. S.; Ch'ng, J.-H.; Quintana, M. d. P.; Vesterlund, M.; Ghorbal, M.; Joannin, N.; Franzen, O.; Lopez-Rubio, J.-J.; Barbieri, S.; Lanzavecchia, A.; Sanyal, S.; Wahlgren, M., *Nature Microbiology* 2017, 2, 17068.
4. Bradbury, E. J.; Moon, L. D.; Popat, R. J.; King, V. R.; Bennett, G. S.; Patel, P. N.; Fawcett, J. W; McMahon, S. B., *Nature* 2002, 416, 636-640.
5. Kyiyata, S.; Komatsu, Y; Yoshimura, Y; Taya, C.; H, K., *Nat. Neurosci.* 2012, 15, 414-422.
6. Brown, J. M.; Xia, J.; Zhuang, B.; Cho, K.-S.; Rogers, C. J.; Gama, C. I.; Rawat, M.; Tully, S. E.; Uetani, N.; Mason, D. E.; Tremblay, M. L.; Peters, E. C.; Habuchi, 0.; Chen, D. F.; Hsieh-Wilson, L. C., *Proc. Natl. Acad. Sci. USA* 2012, 109, 4768-4773.

7. Gama, C.; Tully, S. E.; Sotogaku, N.; Clark, P. M.; Rawat, M.; Vaidehi, N.; Goddard, W. A.; Nishi, A.; Hsieh-Wilson, L. C., *Nat Chem Biol* 2006, 2, 467-473.
8. Yang, X.; Lin, Y P.; Heselpoth, R. D.; Buyuktanir, O.; Qin, J.; Kung, F.; Nelson, D. C.; Leong, J. M.; Pal, U., *Cell Microbiol* 2016, 18, 97-110.
9. Pulsipher, A.; Griffin, M. E.; Stone, S. E.; Brown, J. M.; Hsieh-Wilson, L. C., *J. Am. Chem. Soc.* 2014, 136, 6794-6797.
10. Stabler, T. V.; Huang, Z.; Montell, E.; Verges, J.; Kraus, V. B., *Osteoarthritis and Cartilage* 2017, 25, 166-174.
11. Roman-Blas, J. A.; Mediero, A.; Tardio, L.; Portal-Nunez, S.; Gratal, P.; Herrero-Beaumont, G.; Largo, R., *Eur. J. Pharmacol.* 2017, 794, 8-14.
12. Ly, M.; Leach III, F. E.; Laremore, T. N.; Toida, T.; Amster, I. J.; Linhardt, R. J., *Nat. Chem. Biol.* 2011, 7, 827-833.
13. Tamura, J.-i.; Nakada, Y; Taniguchi, K.; Yamane, M., *Carbohydr. Res.* 2008, 343, 39-47.
14. Lopin-Bon, C.; Jacquinet, J.-C., *Carbohydr. Res.* 2015, 402, 35-43.
15. Miyachi, K.; Wakao, M.; Suda, Y, *Bioorg Med Chem Lett* 2015, 25, 1552-1555.
16. Solera, C.; Macchione, G.; Maza, S.; Kayser, M. M.; Corzana, F.; de Paz, J. L.; Nieto, P. M., *Chemistry* 2016, 22, 2356-2369.
17. Jacquinet, J.-C.; Lopin, C., *Angew. Chem. Int. Ed.* 2006, 45, 2574-2578.
18. Eller, S.; Collot, M.; Yin, J.; Hahm, H. S.; Seeberger, P. H., *Angew. Chem. Int. ed.* 2013, 52, 5858-5861.
19. Sugiura, N.; Shioiri, T; Chiba, M.; Narimatsu, H.; Kimata, K.; Watanabe, H., *J. Biol. Chem.* 2012, 287, 43390-43400.
20. Sugiura, N.; Clausen, T M.; Shioiri, T; Gustavsson, T.; Watanabe, H.; Salanti, A., *Glycoconj J* 2016, in press, DOI 10.1007/s10719-016-9685-z.
21. Shioiri, T.; Tsuchimotot, J.; Watanabe, H.; Sugiura, N., *Glycobiology* 2016, 26, 592-606.
22. Sugiura, N.; Shimokata, S.; Minamisawa, T; Hirabayashi, J.; Kimata, K.; Watanabe, H., *Glycoconj J* 2008, 25, 521-530.
23. Xue, J.; Jin, L.; Zhang, X.; Wang, F.; Ling, P.; Sheng, J., *Biochim Biophys Acta* 2016, 1860, 844-855.
24. Zhao, G.; Guan, W.; Cai, L.; Wang, P. G., *Nat. Protoc.* 2010, 5, 636-646.
25. Bouregeaux, V.; Piller, F.; Piller, V., *Bioorg Med Chem Lett* 2005, 15, 5459-5462.
26. Sugiura, N.; Setoyama, y.; Chiba, M.; Kimata, K.; Watanabe, H., *J. Biol. Chem.* 2011, 286, 29026-29034.
27. Yusa, A.; Kitajima, K.; Habuchi, O., *J. Biol. Chem.* 2006, 281, 20393-20403.

All references listed herein including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A synthetic chondroitin sulfate oligosaccharide, wherein the synthetic chondroitin sulfate oligosaccharide comprises a 4-O-sulfated and/or 6-O-sulfated chondroitin oligosaccharide selected from a chondroitin sulfate D (CS-D) 13-mer, a CS-D 14-mer, and a CS-D 15-mer.

2. A composition comprising one or more synthetic chondroitin sulfate oligosaccharides of claim 1.

3. The composition of claim 2, further comprising a pharmaceutically acceptable carrier.

4. A synthetic chondroitin sulfate oligosaccharide, wherein the synthetic chondroitin sulfate oligosaccharide comprises a 4-O-sulfated and/or 6-O-sulfated chondroitin oligosaccharide selected from a chondroitin sulfate C (CS-C) or a chondroitin sulfate D (CS-D) and having a size ranging from a 13-mer to a 15-mer, and wherein the synthetic chondroitin sulfate oligosaccharide is an unnatural chondroitin sulfate oligosaccharide, wherein the unnatural chondroitin sulfate oligosaccharide comprises a 6-O-sulfo2-azido galactosamine or a 6-O-sulfo galactosamine residue.

5. A synthetic chondroitin sulfate oligosaccha ride, wherein the synthetic chondroitin sulfate oligosaccharide comprises a structure selected from the group consisting of:

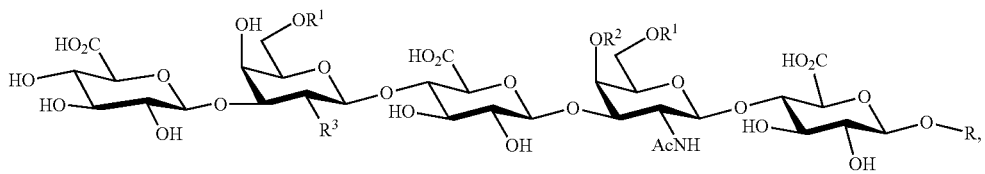

where $R^1=R^2=H$; $R^3=$NHFTA,
where $R^1=SO_3H$; $R^2=H$; $R^3=$NHFTA,
where $R1=R^2=H$; $R^3=NH_2$,
where $R^1=SO_3H$; $R^2=H$; $R^3=NH_2$,
where $R^1=R^2=H$; $R^3=N_3$, or
where $R^1=SO_3H$; $R^2=H$; $R^3=N_3$; and

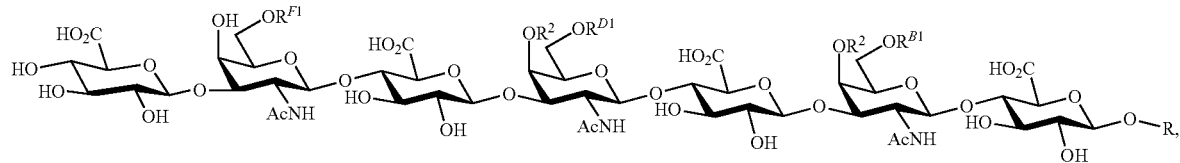

where
$R^{B1}=SO_3H$; $R^{D1}=R^{F1}=R^2=H$; and
wherein R is selected from the group consisting of —H, alkyl, substituted alkyl, aryl, and substituted aryl.

6. The synthetic chondroitin sulfate oligosaccharide of claim 5, wherein the alkyl is —CH_3 or —CH_2CH_3 or the substituted aryl is a p-nitrophenyl group.

7. A composition comprising one or more synthetic chondroitin sulfate oligosaccharides of claim 5.

8. The composition of claim 7, further comprising a pharmaceutically acceptable carrier.

* * * * *